(12) United States Patent
Yamamoto et al.

(10) Patent No.: US 11,696,874 B2
(45) Date of Patent: *Jul. 11, 2023

(54) DENTAL PHOTOCURABLE COMPOSITION EXCELLENT IN COLOR TONE SELECTIVITY

(71) Applicant: SHOFU INC., Kyoto (JP)

(72) Inventors: Kenzo Yamamoto, Kyoto (JP); Hideto Kasaba, Kyoto (JP); Daisuke Hara, Kyoto (JP); Shunsuke Miyata, Kyoto (JP)

(73) Assignee: SHOFU INC., Kyoto (JP)

( * ) Notice: Subject to any disclaimer, the term of this patent is extended or adjusted under 35 U.S.C. 154(b) by 47 days.

This patent is subject to a terminal disclaimer.

(21) Appl. No.: 17/201,180

(22) Filed: Mar. 15, 2021

(65) Prior Publication Data

US 2022/0287921 A1    Sep. 15, 2022

(30) Foreign Application Priority Data

Mar. 12, 2021 (JP) ................. 2021-040033
Mar. 12, 2021 (JP) ................. 2021-040037
Mar. 12, 2021 (JP) ................. 2021-040039
Mar. 12, 2021 (JP) ................. 2021-040040

(51) Int. Cl.
| | |
|---|---|
| *A61K 6/62* | (2020.01) |
| *A61K 6/71* | (2020.01) |
| *A61K 6/78* | (2020.01) |
| *A61K 6/30* | (2020.01) |
| *A61K 6/831* | (2020.01) |
| *A61K 6/887* | (2020.01) |
| *A61K 6/61* | (2020.01) |
| *C08F 220/28* | (2006.01) |
| *C08F 220/32* | (2006.01) |
| *C08F 2/50* | (2006.01) |
| *C08K 5/00* | (2006.01) |
| *C08K 5/08* | (2006.01) |
| *C08K 5/14* | (2006.01) |
| *C08K 5/17* | (2006.01) |

(52) U.S. Cl.
CPC ............ *A61K 6/62* (2020.01); *A61K 6/30* (2020.01); *A61K 6/61* (2020.01); *A61K 6/71* (2020.01); *A61K 6/78* (2020.01); *A61K 6/831* (2020.01); *A61K 6/887* (2020.01); *C08F 2/50* (2013.01); *C08F 220/283* (2020.02); *C08F 220/325* (2020.02); *C08K 5/0025* (2013.01); *C08K 5/08* (2013.01); *C08K 5/14* (2013.01); *C08K 5/17* (2013.01)

(58) Field of Classification Search
CPC ........................................................ A61K 6/62
See application file for complete search history.

(56) References Cited

U.S. PATENT DOCUMENTS

| | | | |
|---|---|---|---|
| 5,846,075 A | 12/1998 | Suh et al. | |
| 7,084,182 B2* | 8/2006 | Hara ................. | A61K 6/884 522/16 |
| 2005/0123762 A1 | 6/2005 | Ori et al. | |
| 2007/0100020 A1 | 5/2007 | Nakatsuka et al. | |
| 2008/0068862 A1 | 3/2008 | Shimura | |
| 2009/0068123 A1 | 3/2009 | Takei et al. | |
| 2010/0267856 A1 | 10/2010 | Shinoda et al. | |
| 2010/0311858 A1 | 12/2010 | Holmes et al. | |
| 2011/0288195 A1 | 11/2011 | Kajikawa et al. | |
| 2017/0355857 A1 | 12/2017 | Lee et al. | |
| 2018/0373145 A1* | 12/2018 | Shiraishi ............ | G03F 7/039 |
| 2019/0388355 A1 | 12/2019 | Christensen et al. | |
| 2020/0069534 A1 | 3/2020 | Furuhashi et al. | |
| 2021/0283022 A1 | 9/2021 | Miyata et al. | |
| 2022/0002453 A1 | 1/2022 | Hayakawa et al. | |

FOREIGN PATENT DOCUMENTS

| | | |
|---|---|---|
| EP | 1 101 484 | 5/2001 |
| EP | 2 163 234 | 3/2010 |
| EP | 2 280 032 | 2/2011 |
| EP | 2 394 628 | 12/2011 |
| EP | 3 398 975 | 11/2018 |

(Continued)

OTHER PUBLICATIONS

English machine translation of Akitsumi et al. (JP 2005-213231) (Year: 2005).*
Extended European Search Report dated Jun. 25, 2021 in corresponding European Patent Application No. 21162475.4.
Extended European Search Report dated Sep. 7, 2021 in corresponding European Patent Application No. 21162481.2.
Extended European Search Report dated Sep. 9, 2021 in corresponding European Patent Application No. 21162479.6.
Extended European Search Report dated Sep. 7, 2021 in corresponding European Patent Application No. 21162490.3.
Extended European Search Report dated Sep. 7, 2021 in corresponding European Patent Application No. 21162495.2.

(Continued)

*Primary Examiner* — Michael F Pepitone
(74) *Attorney, Agent, or Firm* — Wenderoth, Lind & Ponack, L.L.P.

(57) ABSTRACT

[Problem]
To provide a dental photocurable composition having sufficient mechanical property and being excellent in color tone selectivity because of having a small color difference between before curing and after curing.
[Solution]
To provide a dental photocurable composition, comprising (A) polymerizable monomer, (B) photosensitizer, (C) photoacid generator, (D) photopolymerization accelerator and (E) filler, wherein, the dental photocurable composition comprises (B-1) α-diketone compound as the (B) photosensitizer, and the dental photocurable composition comprises, with respect to 100 parts by mass of the (A) polymerizable monomer, 0.15 parts by mass or less of the (B-1) α-diketone compound, 0.5 parts by mass or more of the (C) photoacid generator, and 100 parts by mass or more of the (E) filler.

20 Claims, No Drawings

(56) References Cited

FOREIGN PATENT DOCUMENTS

| EP | 3 782 598 | 2/2021 | |
|---|---|---|---|
| JP | 2001-139843 | 5/2001 | |
| JP | 2005213231 A * | 8/2005 | |
| JP | 2006-76973 | 3/2006 | |
| JP | 2006-225350 | 8/2006 | |
| JP | 4093974 | 3/2008 | |
| JP | 4596786 | 10/2010 | |
| JP | 4783151 | 7/2011 | |
| JP | 5114498 | 10/2012 | |
| JP | 5268478 | 5/2013 | |
| JP | 5379563 | 10/2013 | |
| JP | 5461415 | 1/2014 | |
| JP | 5615720 | 9/2014 | |
| JP | 2017119803 A * | 7/2017 | ............... C08F 2/50 |
| JP | 2020-500879 | 1/2020 | |
| WO | 99/62460 | 12/1999 | |
| WO | 2006/106838 | 10/2006 | |
| WO | 2008/068862 | 6/2008 | |
| WO | 2018/164074 | 9/2018 | |

OTHER PUBLICATIONS

Extended European Search Report dated Aug. 29, 2022 in corresponding European Patent Application No. 22161514.9.
Extended European Search Report dated Aug. 29, 2022 in corresponding European Patent Application No. 22161538.8.
Extended European Search Report dated Aug. 29, 2022 in corresponding European Patent Application No. 22161548.7.
Markus Griesser et al., "Photoinitiators with β-phenylogous Cleavage: an evaluation of reaction mechanisms and performance", Macromolecules, vol. 45, pp. 1737-1745, 2012.

* cited by examiner

DENTAL PHOTOCURABLE COMPOSITION EXCELLENT IN COLOR TONE SELECTIVITY

CROSS-REFERENCE TO RELATED APPLICATIONS

This application is based on and claims the benefit of priorities from Japanese Patent Application Serial No. 2021-40033 (filed on Mar. 12, 2021), Japanese Patent Application Serial No. 2021-40037 (filed on Mar. 12, 2021), Japanese Patent Application Serial No. 2021-40039 (filed on Mar. 12, 2021), and Japanese Patent Application Serial No. 2021-40040 (filed on Mar. 12, 2021), the contents of which are hereby incorporated by reference in their entirety.

BACKGROUND OF THE INVENTION

Field of the Invention

The present disclosure relates to a dental photocurable composition.

Description of the Related Art

A dental photocurable compositions has been used in the dental field, and applied to a dental adhesive material, a dental composite resin, a dental core build-up material, a dental resin cement, a dental coating material, a dental sealant material, a dental manicure material, a dental splinting material, a dental glass ionomer cement, a dental hard resin, a dental CAD-CAM restoration material, a dental 3D printer material and the like.

In Japanese Patent No. 4093974 and Japanese Patent No. 4596786, a photopolymerization initiator comprising a photoacid generator (triazine compound or specific aryliodonium salt), a sensitizer, and an electron donor compound is proposed as a photopolymerization initiator.

In Japanese Patent No. 5114498, two-packs type dental cement in which the compounding amount of α-diketones is limited is proposed.

SUMMARY OF THE INVENTION

Technical Problem

However, in these dental photocurable compositions, a difference in color tone between before curing and after curing is large, and it has been difficult to select an appropriate color tone based on the color tone of the dental photocurable composition before curing, and it has been difficult to exhibit sufficient mechanical properties when the compounding amount of the photosensitizer was reduced in order to reduce the difference in color tone between before curing and after curing.

An object of the present disclosure is to provide a dental photocurable composition having sufficient mechanical property and being excellent in color tone selectivity because of having a small color difference between before curing and after curing.

Solution to Problem

A dental photocurable composition of the present disclosure comprises (A) polymerizable monomer, (B) photosensitizer, (C) photoacid generator, (D) photopolymerization accelerator and (E) filler, wherein, the dental photocurable composition comprises (B-1) α-diketone compound as the (B) photosensitizer, and the dental photocurable composition comprises, with respect to 100 parts by mass of the (A) polymerizable monomer, 0.15 parts by mass or less of the (B-1) α-diketone compound, 0.5 parts by mass or more of the (C) photoacid generator, and 100 parts by mass or more of the (E) filler.

Advantageous Effects of Invention

The dental photocurable composition of the present disclosure has sufficient mechanical property and is excellent in color tone selectivity because of having a small color difference between before curing and after curing.

DETAILED DESCRIPTION OF THE PREFERRED EMBODIMENTS

In the present disclosure, the (B-1) α-diketone compound may be a camphorquinone compound.

In the present disclosure, the dental photocurable composition may comprise an aryl iodonium salt as the (C) photoacid generator, wherein the aryl iodonium salt may be a salt of an anion having an organic group and one or more atoms of P, B, Al, S and Ga, and an aryl iodonium cation.

In the present disclosure, the dental photocurable composition may comprise an aryl iodonium salt as the (C) photoacid generator, wherein the aryl iodonium salt may be a salt of an anion having an organic group in which at least one H may be substituted with F and one or more atoms of P, B, Al, S and Ga, and an aryl iodonium cation.

In the present disclosure, the dental photocurable composition may comprise (D-1) aliphatic tertiary amine compound not having two or more primary hydroxy groups as (D) photopolymerization accelerator.

In the present disclosure, the dental photocurable composition may comprise, with respect to 100 parts by mass of the (A) polymerizable monomer, 1 parts by mass or more of the (C) photoacid generator, and 0.5 parts by mass or more of the (D) photopolymerization accelerator.

In the present disclosure, a difference between b* value before curing which may be obtained by color measuring a color tone in the L*a*b* color space for a 1-mm-thick dental photocurable composition (or a dental photocurable composition in which a pigment is excluded when the dental photocurable composition contains the pigment) on a white background and b* value after curing which may be obtained by color measuring a color tone in the L*a*b* color space for a 1-mm-thick cured body of the dental photocurable composition on a white background may be 5 or less.

In the present disclosure, the dental photocurable composition may be one pack type dental photocurable composition comprising, with respect to 100 parts by mass of the (A) polymerizable monomer, 0.005 to 0.15 parts by mass of the (B-1) α-diketone compound, 0.5 to 10 parts by mass of the (C) photoacid generator, 0.1 to 10.0 parts by mass of the (D) photopolymerization accelerator, and 150 to 1000 parts by mass or more of the (E) filler.

In the present disclosure, the dental photocurable composition may be two packs type dental photocurable composition consisting of a first paste and a second paste, wherein the first paste may include a first matrix containing the (A) polymerizable monomer, the (B-1) α-diketone compound, the (C) photoacid generator and the (D) photopolymerization accelerator, and the (E) filler, the second paste may include a second matrix containing the (A) polymerizable monomer, the (B-1) α-diketone compound, the (C)

photoacid generator and the (D) photopolymerization accelerator, and the (E) filler, a specific gravity of the first paste and the second paste may be 1:0.8 to 1:1.2, the dental photocurable composition may comprise, with respect to 200 parts by mass of total of the (A) polymerizable monomer contained in the first matrix and the second matrix, 0.01 to 0.3 parts by mass of the (B-1) α-diketone compound, 1.0 to 20.0 parts by mass of the (C) photoacid generator, 0.2 to 20.0 parts by mass of the (D) photopolymerization accelerator, and 200 to 800 parts by mass or more of the (E) filler.

In the present disclosure, the dental photocurable composition may constitute a dental kit by using in combination with a dental composition used for checking color conformity.

Hereinafter, each component in the dental photocurable composition of the present disclosure is described in detail. The dental photocurable composition of the present disclosure is applied as a dental adhesive material, a dental composite resin, a dental core build-up material, a dental resin cement, a dental coating material, a dental sealant material, a dental manicure material, a dental splinting material, a dental glass ionomer cement, a dental hard resin, a dental CAD-CAM restoration material, a dental 3D printer material and the like.

In a dental practice, in order to restore aesthetically and functionally a lost portion of a tooth by caries, breakages and the like, a direct restoration by a dental composite resin and an indirect restoration by a prosthetic device consisting of ceramics or dental hard resin by using a dental resin cement have been performed as treatment. In addition, a dental adhesive material for adhering a dental composite resin and various dental materials and a natural tooth, a dental splinting material for fixing a mobile tooth, a dental coating material for protecting a vital tooth after forming, against a hyperesthesia, an external stimulation and secondary caries, a dental sealant material for preventing caries by filling complex grooves such as especially a deciduous tooth, a dental manicure material for temporary recovering aesthetic property by masking discoloration of a tooth, and a dental core build-up material for forming an abutment tooth in the case of collapsing of a dental crown due to caries have been used. In recent years, new composite materials such as a dental CAD-CAM restoration material for preparing a prosthetic device by CAD/CAM processing and a dental 3D printer material for preparing a prosthetic device by 3D printer have been developed, and various dental materials have been used for treatment. The above-described materials are prepared into a uniform paste by mixing a resin matrix consisting of several kinds of polymerizable monomers, a filler such as an inorganic filler and an organic-inorganic composite filler, and a polymerization initiator, according to the application. As one example of some materials, a dental composite resin for filling is used by filling into a tooth in the form of uncured paste, imparting anatomical form of a natural tooth with a dental instrument such as an instrument, and curing by irradiating light with a light irradiator or the like. For the irradiation light from a light irradiator, a light source having an output of about 100 to 2000 mW/cm$^2$ in a wavelength range of about 360 to 500 nm is generally used. On the other hand, a dental resin cement is used for adhering a prosthetic device to a tooth cavity or an abutment tooth, and is cured by light irradiation after attaching the prosthetic device to the tooth cavity or the abutment tooth.

As the photopolymerization initiator used for such dental materials, a photosensitizer and a system in which a photosensitizer is combined with an appropriate photopolymerization accelerator has been widely used. As the photosensitizer, acylphosphine oxide compounds and α-diketone compounds are known, and in particular, α-diketone compounds have an ability to initiate polymerization in the wavelength range of visible light which has little effect on the human body. Furthermore, α-diketone compounds have photobleaching ability, and since the original color tone of yellow disappears after light irradiation, it has an advantage that the color tone affinity with respect to the white tooth substance is particularly high.

A tertiary amine compound is well known as a polymerization accelerator to be combined with a photosensitizer, and a combination of an α-diketone compound and a tertiary amine compound has high polymerization activity with respect to irradiation light, and thus has been used in a dental material field. The dental photocurable composition containing this photopolymerization initiator exhibits excellent mechanical properties such as hardness, flexural strength, and compressive strength required for various materials.

However, the photopolymerization initiator that has been used conventionally has a problem in that the color tone differs between before curing and after curing because the amount of the photosensitizer compounded is large. For example, since it is difficult to imagine the color tone of a composite resin after curing in the case of filling the composite resin, there is a risk that the operator makes a mistake in selecting the color tone. Further, when there is uneven curing in the dental photocurable composition filled in the deep part of the tooth cavity, the color tone compatibility becomes insufficient.

For dental cement, try-in paste is also used in cases where high aesthetic property is required, such as a prosthetic device made of ceramics and a case where a laminate veneer is used. By using at a try-in stage, the color tone of the prosthetic device or a dental cement to be used finally is selected. Since the try-in paste is used to confirm the final luting state of the prosthetic device, it is prepared so as to have the same color tone as the dental photocurable composition after curing. Therefore, when the color tone of the dental photocurable composition before curing is different from the color tone after curing, the color tone of the try-in paste also differs, and therefore there is a case that the operator may misidentify the color tone selection error.

From these facts, for example, in the conventional photopolymerization initiator system, the change in color tone before curing and after curing can be reduced by reducing the compounding amount of the photosensitizer. However, in such a case, curing does not proceed sufficiently and therefore it is difficult to exhibit sufficient mechanical strength to withstand the use as dental materials.

In order to solve the above problems, it has been found that the dental photocurable composition of the present disclosure exhibits good mechanical property by the combined use of a photoacid generator and a photopolymerization accelerator while containing α-diketones as a photosensitizer in a smaller amount than before, and the present disclosure has been completed. That is, when the dental photocurable composition of the present disclosure is used, it is expected that the operator can easily imagine the color tone after curing from the stage before light irradiation and excellent color tone compatibility with the tooth is exhibited. Further, since the color tones of the dental photocurable composition before curing and after curing are in the same degree as that of the try-in paste, a dental cement kit combining these can be expected to reduce the operator's mistake in selecting the color tone.

As the (A) polymerizable monomer of the present disclosure, any polymerizable monomers can be used without limitation as long as it is known. In the polymerizable monomer or the compound having a polymerizable group described in the present disclosure, the polymerizable group preferably exhibits radical polymerizability, and specifically, from the viewpoint of easy radical polymerization, the polymerizable group is preferably (meth) acrylic group and/or (meth) acrylamide group. In the present specification, "(meth) acrylic" means acrylic and/or methacrylic, "(meth) acryloyl" means acryloyl and/or methacryloyl, "(meth) acrylate" means acrylate and/or methacrylate, and, "(meth) acrylamide" means acrylamide and/or methacrylamide. A polymerizable monomer having a substituent at the α-position of an acrylic group and/or an acrylamide group can also be preferably used. Specific examples include one having one radical polymerizable group, one having two radical polymerizable groups, one having three or more radical polymerizable groups, one having an acidic group, one having an alkoxysilyl group, and one having a sulfur atom.

Specific examples of a polymerizable monomer having one radical polymerizable group and not containing acidic group include 2-hydroxyethyl (meth) acrylate, 3-hydroxypropyl (meth) acrylate, 4-hydroxybutyl (meth) acrylate, 2-hydroxypropyl (meth) acrylate, 2-hydroxybutyl (meth) acrylate, 6-hydroxyhexyl (meth) acrylate, 10-hydroxydecyl (meth) acrylate, propylene glycol mono (meth) acrylate, glycerol mono (meth) acrylate, erythritol mono (meth) acrylate, N-methylol (meth) acrylamide, N-hydroxyethyl (meth) acrylamide, N,N-(dihydroxyethyl) (meth) acrylamide, methyl (meth) acrylate, ethyl (meth) acrylate, propyl (meth) acrylate, isopropyl (meth) acrylate, butyl (meth) acrylate, isobutyl (meth) acrylate, benzyl (meth) acrylate, lauryl (meth) acrylate, 2,3-dibromopropyl (meth) acrylate, 3-(meth) acryloyloxypropyl trimethoxysilane, 11-(meth) acryloyloxyundecyl trimethoxysilane, (meth) acrylamide and the like.

Specific Examples of the polymerizable monomer having two radical polymerizable groups and not containing acidic group include 2,2-bis ((meth) acryloyloxy phenyl) propane, 2,2-bis [4-(3-(meth) acryloyloxy)-2-hydroxy propoxyphenyl] propane (generally called "Bis-GMA"), 2,2-bis (4-(meth) acryloyloxy phenyl) propane, 2,2-bis (4-(meth) acryloyloxy polyethoxyphenyl) propane, 2,2-bis (4-(meth) acryloyloxy diethoxyphenyl) propane, 2,2-bis (4-(meth) acryloyloxy tetraethoxyphenyl) propane, 2,2-bis (4-(meth) acryloyloxy pentaethoxyphenyl) propane, 2,2-bis (4-(meth) acryloyloxy dipropoxyphenyl) propane, 2-(4-(meth) acryloyloxy diethoxyphenyl)-2-(4-(meth) acryloyloxy diethoxyphenyl) propane, 2-(4-(meth) acryloyloxy diethoxyphenyl)-2-(4-(meth) acryloyloxy ditriethoxyphenyl) propane, 2-(4-(meth) acryloyloxy dipropoxyphenyl)-2-(4-(meth) acryloyloxy triethoxyphenyl) propane, 2,2-bis (4-(meth) acryloyloxy propoxyphenyl) propane, 2,2-bis (4-(meth) acryloyloxy isopropoxyphenyl) propane, 1,4-bis (2-(meth) acryloyloxyethyl) pyromellitate, glycerol di (meth) acrylate, 1-(acryloyloxy)-3-(methacryloyloxy)-2-propanol, ethyleneglycol di (meth) acrylate, diethylene glycol di (meth) acrylate, triethylene glycol di (meth) acrylate, propylene glycol di (meth) acrylate, butylene glycol di (meth) acrylate, neopentyl glycol di (meth) acrylate, polyethylene glycol di (meth) acrylate, 1,3-butanediol di (meth) acrylate, 1,5-pentanediol di (meth) acrylate, 1,6-hexanediol di (meth) acrylate, 1,10-decanediol di (meth) acrylate, 1,2-bis (3-methacryloyloxy-2-hydroxypropoxy) ethane, 2,2,4-trimethyl hexamethylene bis (2-carbamoyloxy ethyl) dimethacrylate (generally called "UDMA"), 1,2-bis (3-methacryloyloxy-2-hydroxy propoxy) ethane and the like.

Specific Examples of the polymerizable monomer having three or more radical polymerizable groups and not containing acidic group include trimethylolpropane tri (meth) acrylate, trimethylolethane tri (meth) acrylate, trimethylolmethane tri (meth) acrylate, pentaerythritol tri (meth) acrylate, pentaerythritol tetra (meth) acrylate, dipentaerythritol penta (meth) acrylate, N,N-(2,2,4-trimethyl hexamethylene) bis [2-(aminocarboxy) propane-1,3-diol] tetra methacrylate, 1,7-diacryloyloxy-2,2,6,6-tetra acryloyloxymethyl-4-oxyheptane and the like.

For the polymerizable monomer having an acidic group, any polymerizable monomer can be used without any limitation as long as it has one or more polymerizable group and at least one acidic group such as a phosphoric acid group, a pyrophosphoric acid group, a thiophosphoric acid group, a phosphonic acid group, a sulfonic acid group and a carboxylic acid group and the like.

Specific examples of a phosphoric acid group-containing polymerizable monomer include 2-(meth) acryloyloxyethyl dihydrogen phosphate, 3-(meth) acryloyloxypropyl dihydrogen phosphate, 4-(meth) acryloyloxybutyl dihydrogen phosphate, 5-(meth) acryloyloxypentyl dihydrogen phosphate, 6-(meth) acryloyloxyhexyl dihydrogen phosphate, 7-(meth) acryloyloxyheptyl dihydrogen phosphate, 8-(meth) acryloyloxyoctyl dihydrogen phosphate, 9-(meth) acryloyloxynonyl dihydrogen phosphate, 10-(meth) acryloyloxydecyl dihydrogen phosphate, 11-(meth) acryloyloxyundecyl dihydrogen phosphate, 12-(meth) acryloyloxydodecyl dihydrogen phosphate, 16-(meth) acryloyloxyhexadecyl dihydrogen phosphate, 20-(meth) acryloyloxyicosyl dihydrogen phosphate, bis [2-(meth) acryloyl oxyethyl]hydrogensphosphate, bis [4-(meth) acryloyl oxybutyl] hydrogen phosphate, bis [6-(meth) acryloyl oxyhexyl] hydrogen phosphate, bis [8-(meth) acryloyl oxyoctyl] hydrogen phosphate, bis [9-(meth) acryloyl oxynonyl] hydrogen phosphate, bis [10-(meth) acryloyl oxydecyl] hydrogen phosphate, 1,3-di (meth) acryloyl oxypropyl dihydrogenphosphate, 2-(meth) acryloyl oxyethylphenyl hydrogen phosphate, 2-(meth) acryloyloxyethyl-2-bromoethyl hydrogen phosphate and bis [2-(meth) acryloyloxy-(1-hyrdoxymethyl) ethyl]hydrogen phosphate; acyl chloride, alkali metal salt and ammonium salt thereof; and (meth) acrylamide compound in which the ester bond of these compounds is substituted with an amide bond, and the like.

Specific examples of a pyrophosphoric acid group-containing polymerizable monomer include bis [2-(meth) acryloyl oxyethyl] pyrophosphate, bis [4-(meth) acryloyl oxybutyl] pyrophosphate, bis [6-(meth) acryloyl oxyhexyl] pyrophosphate, bis [8-(meth) acryloyl oxyoctyl] pyrophosphate, bis [10-(meth) acryloyl oxydecyl] pyrophosphate; acyl chloride, alkali metal salt and ammonium salt thereof; and (meth) acrylamide compound in which the ester bond of these compounds is substituted with an amide bond, and the like.

Specific examples of a thiophosphate group-containing polymerizable monomer include 2-(meth) acryloyloxyethyl dihydrogen thiophosphate, 3-(meth) acryloyloxypropyl dihydrogen thiophosphate, 4-(meth) acryloyloxybutyl dihydrogen thiophosphate, 5-(meth) acryloyloxypentyl dihydrogen thiophosphate, 6-(meth) acryloyloxyhexyl dihydrogen thiophosphate, 7-(meth) acryloyloxyheptyl dihydrogen thiophosphate, 8-(meth) acryloyloxyoctyl dihydrogen thiophosphate, 9-(meth) acryloyloxynonyl dihydrogen thiophosphate, 10-(meth) acryloyloxydecyl dihydrogen thiophosphate, 11-(meth) acryloyloxyundecyl dihydrogen thiophosphate, 12-(meth) acryloyloxydodecyl dihydrogen thiophosphate, 16-(meth) acryloyloxyhexadecyl dihydrogen thiophosphate, 20-(meth) acryloyloxyicosyl dihydrogen thiophosphate; acyl chloride, alkali metal salt and ammonium salt thereof; and (meth) acrylamide compound in which the ester bond of these compounds is substituted with an amide bond, and the like. The polymerizable monomer having a thiophosphate group is also classified as a polymerizable monomer having a sulfur atom.

Specific examples of a phosphonic acid group-containing polymerizable monomer include 2-(meth) acryloyloxy ethylphenyl phosphonate, 5-(meth) acryloyloxy pentyl-3-phosphonopropionate, 6-(meth) acryloyloxy hexyl-3-phosphonopropionate, 10-(meth) acryloyloxy decyl-3-phosphonopropionate, 6-(meth) acryloyloxy hexyl-3-phosphonoacetate, 10-(meth) acryloyloxy decyl-3-phosphonoacetate; acyl chloride, alkali metal salt and ammonium salt thereof; and (meth)acrylamide compound in which the ester bond of these compounds is substituted with an amide bond, and the like.

Specific examples of a sulfonic acid group-containing polymerizable monomer include 2-(meth) acrylamide-2-methyl propanesulfonic acid and 2-sulfoethyl (meth) acrylate and the like.

The carboxylic acid group-containing polymerizable monomers are classified into a (meth) acrylic-based compound having one carboxyl group in the molecule and a (meth) acrylic-based compound having a plurality of carboxyl groups in the molecule. Examples of the (meth) acrylic-based compound having one carboxyl group in the molecule include (meth) acrylic acid, N-(meth) acryloyl glycine, N-(meth) acryloyl aspartic acid, 0-(meth) acryloyl tyrosine, N-(meth) acryloyl tyrosine, N-(meth) acryloyl phenylalanine, N-(meth) acryloyl-p-aminobenzoic acid, N-(meth) acryloyl-o-aminobenzoic acid, p-vinylbenzoic acid, 2-(meth) acryloyloxybenzoic acid, 3-(meth) acryloyloxybenzoic acid, 4-(meth) acryloyloxybenzoic acid, N-(meth) acryloyl-5-aminosalicylic acid, N-(meth) acryloyl-4-aminosalicylic acid, 2-(meth) acryloyloxyethyl hydrogen succinate, 2-(meth) acryloyloxyethyl hydrogen phthalate, 2-(meth) acryloyloxyethyl hydrogenmalate; acyl chloride thereof; and (meth)acrylamide compound in which the ester bond of these compounds is substituted with an amide bond, and the like. Examples of the (meth) acrylic-based compound having a plurality of carboxyl groups in the molecule include 6-(meth) acryloyl oxyhexane-1,1-dicarboxylic acid, 9-(meth) acryloyl oxynonane-1,1-dicarboxylic acid, 10-(meth) acryloyl oxydecane-1,1-dicarboxylic acid, 11-(meth) acryloyloxy undecane-1,1-dicarboxylic acid, 12-(meth) acryloyl oxydodecane-1,1-dicarboxylic acid, 13-(meth) acryloyloxy tridecane-1,1-dicarboxylic acid, 4-(meth) acryloyloxyethyl trimeritate, 4-(meth) acryloyloxybutyl trimeritate, 4-(meth) acryloyloxyhexyl trimeritate, 4-(meth) acryloyloxydecyl trimeritate, 2-(meth) acryloyl oxyethyl-3'-(meth) acryloyloxy-2'-(3,4-dicarboxy benzoyloxy) propylsuccinate; acid anhydrides and acid halides thereof; and (meth) acrylamide compound in which the ester bond of these compounds is substituted with an amide bond, and the like.

Specific examples of the polymerizable monomer having an alkoxysilyl group include a (meth) acrylic compound having one alkoxysilyl group in the molecule and a (meth) acrylic compound having a plurality of alkoxysilyl groups in the molecule. Specific examples include 2-(meth) acryloxyethyl trimethoxysilane, 3-(meth) acryloxypropyl trimethoxysilane, 3-(meth) acryloxypropyl triethoxysilane, 3-(meth) acryloxypropyl methyldimethoxysilane, 4-(meth) acryloxybutyl trimethoxysilane, 5-(meth) acryloxypentyl trimethoxysilane, 6-(meth) acryloxyhexyl trimethoxysilane, 7-(meth) acryloxyheptyl trimethoxysilane, 8-(meth) acryloxyoctyl trimethoxysilane, 9-(meth) acryloxynonyl trimethoxysilane, 10-(meth) acryloxydecyl trimethoxysilane, 11-(meth) acryloxyundecyl trimethoxysilane.

As the polymerizable monomer having a sulfur atom, any known compound can be used without any limitation as long as it is a polymerizable monomer having one or more sulfur atoms and a polymerizable group. Specifically, it refers to a compound having a partial structure such as $-SH$, $-S-S-$, $>C=S$, $>C-S-C<$, $>P=S$, or a compound prepared by tautomerism. Specific examples include 10-methacryloxy decyl-6,8-dithiooctanate, 6-methacryloxy hexyl-6,8-dithiooctanate, 6-methacryloxy hexyl-2-thiouracil-5-carboxylate, 2-(11-methacryloxy undecylthio)-5-mercapto-1,3,4-thiadiazole, 10-(meth) acryloxy decyl dihydrogenthiophosphate.

An oligomer or a prepolymer having at least one polymerizable group in its molecule may be used other than such a polymerizable monomer, without any limitation. There is no problem even if a substituent such as a fluoro group is contained in the same molecule. The polymerizable monomers described above can be used not only singly but also in combinations of a plurality thereof.

The dental photocurable composition of the present disclosure may contain a known polymerizable monomer having an acidic group as the (A) polymerizable monomer in order to impart adhesive property with respect to a tooth substance and a prosthetic device. Among them, 10-methacryloyloxydecyl dihydrogenphosphate and 6-methacryloxyhexyl phosphonoacetate are preferable. From the view point of imparting adhesive property, the compounding amount of the polymerizable monomer having an acidic group is, with respect to 100 parts by mass of the total amount of the polymerizable monomer contained in the dental photocurable composition, 1 part by mass or more, preferably 10 parts by mass or more.

The dental photocurable composition of the present disclosure may contain a silane coupling agent as the (A) polymerizable monomer in order to impart adhesive property with respect to glass ceramics. Any known silane coupling agent can be used without any limitation, but 3-methacryloxypropyl trimethoxysilane, 8-methacryloxyoctyl trimethoxysilane, and 11-methacryloxyundecyl trimethoxysilane are preferable. From the viewpoint of imparting adhesive property, the compounding amount is, with respect to 100 parts by mass of the total amount of the polymerizable monomer contained in the photocurable composition, preferably 1 part by mass or more, more preferably 10 parts by mass or more and less than 20 parts by mass. Since the purpose of the silane coupling agent as a polymerizable monomer is to impart adhesive property with respect to glass ceramics or a resin material containing a filler consisting of glass ceramics, the silane coupling agent is compounded separately from the surface treatment agent of the filler.

The dental photocurable composition of the present disclosure may contain a polymerizable monomer having a sulfur atom as the (A) polymerizable monomer in order to impart adhesive property with respect to a noble metal. From the view point of imparting adhesive property, the compounding amount of the polymerizable monomer having a sulfur atom is, with respect to 100 parts by mass of the total amount of the polymerizable monomer contained in the dental photocurable composition, 0.01 part by mass or more, preferably 0.1 parts by mass or more and less than 10 parts by mass.

<Photopolymerization Initiator>

The photopolymerization initiator used in the dental photocurable composition of the present disclosure includes (B) photosensitizer, (C) photoacid generator, and (D) photopolymerization accelerator and these are not particularly limited, and any known compounds commonly used may be used without any limitation.

[(B) Photosensitizer]

Specific examples of the (B) photosensitizer which can be used in the present disclosure include α-diketones such as benzil, camphorquinone, camphorquinone carboxylic acid, camphorquinone sulfonic acid, α-naphthyl, acetonaphthene, p,p'-dimethoxybenzyl, p,p'-dichlorobenzylacetyl, pentanedion, 1,2-phenanthrenequinone, 1,4-phenanthrenequinone, 3,4-phenanthrenequinone, 9,10-phenanthrenequinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphine oxides such as bis (2,6-dimethoxy benzoyl) phenylphosphine oxide, bis (2,6-dimethoxy benzoyl) (2,4,4-trimethyl pentyl) phosphine oxide, bis (2,6-dimethoxy benzoyl)-n-butylphosphine oxide, bis (2,6-dimethoxy benzoyl)-(2-methylprop-1-yl) phosphine oxide, bis (2,6-dimethoxy benzoyl)-(1-methylprop-1-yl) phosphine oxide, bis (2,6-dimethoxy benzoyl)-t-butyl phosphine oxide, bis (2,6-dimethoxy benzoyl) cyclohexyl phosphine oxide, bis (2,6-dimethoxy benzoyl) octyl phosphine oxide, bis (2-methoxy benzoyl) (2-methylprop-1-yl) phosphine oxide, bis (2-methoxy benzoyl) (1-methylprop-1-yl) phosphine oxide, bis (2,6-diethoxy benzoyl) (2-methylprop-1-yl) phosphine oxide, bis (2,6-diethoxybenzoyl) (1-methylprop-1-yl) phosphine oxide, bis (2,6-dibutoxy benzoyl) (2-methylprop-1-yl) phosphine oxide, bis (2,4-dimethoxy benzoyl) (2-methylprop-1-yl) phosphine oxide, bis (2,4,6-trimethyl benzoyl) phenyl phosphine oxide, 2,4,6-trimethyl benzoyl diphenyl phosphine oxide, bis (2,4,6-trimethyl benzoyl) (2,4-dipentoxy phenyl) phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, bis (2,6-dimethoxy benzoyl) benzyl phosphine oxide, bis (2,6-dimethoxy benzoyl)-2-phenylpropyl phosphine oxide, bis (2,6-dimethoxy benzoyl)-2-phenylethyl phosphine oxide, 2,6-dimethoxy benzoyl benzyl butyl phosphine oxide, 2,6-dimethoxy benzoyl benzyl octyl phosphine oxide, bis (2,4,6-trimethyl benzoyl) isobutyl phosphine oxide and 2,6-dimethoxy benzoyl-2,4,6-trimethyl benzoyl-n-butyl phosphine oxide; acylgermanium compounds such as bisbenzoyl diethylgermanium, bisbenzoyl dimethylgermanium, bisbenzoyl dibutylgermanium, bis (4-methoxybenzoyl) dimethylgermanium and bis (4-methoxybenzoyl) diethylgermanium; α-aminoacetophenones such as 2-benzyl-dimethylamino-1-(4-morpholinophenyl)-butanone-1, and 2-benzyl-diethylamino-1-(4-morpholinophenyl)-propanone-1; ketals such as benzyl dimethyl ketal, benzyl diethyl ketal and benzyl (2-methoxyethyl ketal); and titanocenes such as bis (cyclopentadienyl)-bis [2,6-difluoro-3-(1-pyrrolyl) phenyl]-titanium, bis (cyclopentadienyl)-bis (pentanefluorophenyl)-titanium and his (cyclopentadienyl)-bis (2,3,5,6-tetrafluoro-4-disiloxyphenyl)-titanium.

The photosensitizer (B) may be appropriately selected according to the wavelength, the intensity and the irradiation time of light used for polymerization, and the type and the compounding amount of other components to be combined. In addition, the photosensitizer may be used not only singly but also in combinations of two or more.

[(B-1) α-Diketone Compounds]

The dental photopolymerization composition of the present disclosure contains (B-1) α-diketone compounds as (B) photosensitizer. By using the (B-1) α-diketone compound in combination with the (C) photoacid generator and (D) photopolymerization accelerator, radical polymerization proceeds during light irradiation. It has been found that, with respect to 100 parts by mass of total amount of the polymerizable monomer, even when the compounding amount of the (B-1) α-diketone compound is small, that is, 0.15 parts by mass or less, radical polymerization proceeds to exhibit sufficient mechanical strength that can withstand dental use by compounding 0.5 parts by mass of the (C) photoacid generator and compounding (D) photopolymerization accelerator simultaneously. Further, although the color tone of the dental photocurable composition before curing becomes yellow due to the compounding the (B-1) α-diketone compound, since the content to be compounded of (B-1) α-diketone compound in the dental photopolymerization composition of the present disclosure is smaller than before, the yellowish color of the dental photocurable composition before curing is reduced. Therefore, even when the color tone of the (B-1) α-diketone compound changes after radical polymerization, the color difference becomes small because the compounding amount is small. Thus, it becomes easier for the operator who discharges the paste or the like to imagine the color tone after curing, and the risk of making a mistake in selecting the color tone can be expected to be reduced. Further, the compounding amount of the (B-1) α-diketone compound is the required minimum. Therefore, even if there is uneven curing in the dental photocurable composition filled in the deep part of the tooth cavity, since the color difference between before curing and after curing is small, high color tone compatibility can be expected. In addition, since the compounding amount of the (B-1) α-diketone compound that causes a decrease in light color stability is small, high light color stability can be expected without adding a large amount of an ultraviolet absorber.

Examples of α-diketone compounds include benzyl, camphorquinone, camphorquinone carboxylic acid, camphorquinone sulfonic acid, α-naphthyl, acetonaphthene, p,p'-dimethoxybenzyl, p,p'-dichlorobenzylacetyl, pentandione, 1,2-phenanthrenequinone, 1,4-phenanthrenequinone, 3,4-phenanthrenequinone, 9,10-phenanthrenequinone, and naphthoquinone. Among these, camphorquinone compounds such as camphorquinone, camphorquinone carboxylic acid and camphorquinone sulfonic acid are preferable, and camphorquinone is particularly preferable.

In the dental photocurable composition of the present disclosure, the compounding amount of the (B-1) α-diketone compound with respect to 100 parts by mass of the total amount of the (A) polymerizable monomer contained in the composition is 0.15 parts by mass or less, preferably 0.005 to 0.15 parts by mass, more preferably 0.01 to 0.15 parts by mass, and further preferably 0.05 to 0.12 parts by mass. In the case of containing more than 0.15 parts by mass, the color difference between before curing and after curing becomes large. By containing 0.005 parts by mass or more, sufficient mechanical properties can be reliably exhibited. Further, a plurality of (B-1) α-diketone compounds may be used in combination.

The dental photocurable composition of the present disclosure may contain only the (B-1) α-diketone compounds as the (B) photosensitizer. When (B) photosensitizer other than (B-1) α-diketone compounds is contained, the compounding amount is preferably 0.001 to 1.0 parts by mass with respect to 100 parts by mass of the total amount of (A) polymerizable monomer. The (B) photosensitizer having strong absorption between the wavelengths of 400 to 500 nm which is the wavelength of a light source widely used in dental applications often has a strong yellow color tone, and therefore the compounding amount is more preferably 0.001 to 0.2 parts by mass. On the other hand, the (B) photosensitizer not having strong absorption between the wavelengths of 400 to 500 nm often has a weak yellow color tone, and therefore the compounding amount is more preferably 0.001 to 0.5 parts by mass. In addition, some (B) photosensitizers do not have photobleaching ability. In such a case, the difference in color tone (difference in b*) between before curing and after curing does not increase even when the compounding amount of the (B) photosensitizer is large. However, the yellowness of the composition both before curing and after curing increases, therefore there is a case that color tone compatibility may deteriorate and ambient light stability may decrease in the case of applying to a repair site where white color is preferred in particular. The tendency of increasing in yellowness is remarkable in (B) photosensitizer having strong absorption between 400 to 500 nm. Since the (B-1) α-diketone compound represented by camphorquinone has a good photobleaching ability, it is preferable because the color tone derived from the (B-1) α-diketone compound is reduced. In addition, since the sensitizing effect on the photoacid generator is high, it is preferable as compared with (B) photosensitizer other than (B-1) α-diketone compounds.

[(C) Photoacid Generator]

As the (C) photoacid generator used in the dental photo-curable composition of the present disclosure, known compounds can be used without limitation. Specific examples include triazine compounds, iodonium salt compounds, sulfonium salt compounds, and sulfonic acid ester compounds. Among these, triazine compounds and iodonium salt-based compounds are preferable because of having high polymerizability in the case of using in combination with a sensitizer. Iodonium salt-based compounds are more preferable. Iodonium-based salt compounds are susceptible to sensitization by photosensitizers that have absorption in the visible light region.

Specific examples of the triazine compound include 2,4,6-tris (trichloro methyl)-s-triazine, 2,4,6-tris (tribromo methyl)-s-triazine, 2-methyl-4,6-bis (trichloro methyl)-s-triazine, 2-methyl-4,6-bis (tribromo methyl)-s-triazine, 2-phenyl-4,6-bis (trichloro methyl)-s-triazine, 2-(p-methoxy phenyl)-4,6-bis (trichloro methyl)-s-triazine, 2-(p-methyl thiophenyl)-4,6-bis (trichloro methyl)-s-triazine, 2-(p-chloro phenyl)-4,6-bis (trichloro methyl)-s-triazine, 2-(2,4-dichloro phenyl)-4,6-bis (trichloro methyl)-s-triazine, 2-(p-bromo phenyl)-4,6-bis (trichloro methyl)-s-triazine, 2-(p-tolyl)-4,6-bis (trichloro methyl)-s-triazine, 2-n-propyl-4,6-bis (trichloro methyl)-s-triazine, 2-(α,α,β-trichloro ethyl)-4,6-bis (trichloro methyl)-s-triazine, 2-styryl-4,6-bis (trichloro methyl)-s-triazine, 2-[2-(p-methoxy phenyl) ethenyl]-4,6-bis (trichloro methyl)-s-triazine, 2-[2-(o-methoxy phenyl) ethenyl]-4,6-bis (trichloro methyl)-s-triazine, 2-[2-(p-butoxy phenyl) ethenyl]-4,6-bis (trichloro methyl)-s-triazine, 2-[2-(3,4-dimethoxy phenyl) ethenyl]-4,6-bis (trichloro methyl)-s-triazine, 2-[2-(3,4,5-trimethoxy phenyl) ethenyl]-4,6-bis (trichloro methyl)-s-triazine, 2-(1-naphthyl)-4,6-bis (trichloro methyl)-s-triazine, 2-(4-biphenylyl)-4,6-bis (trichloro methyl)-s-triazine, 2-[2-{N,N-bis(2-hydroxy ethyl) amino} ethoxy]-4,6-bis (trichloro methyl)-s-triazine, 2-[2-{N-hydroxy ethyl-N-ethylamino} ethoxy]-4,6-bis (trichloro methyl)-s-triazine, 2-[2-{N-hydroxy ethyl-N-methylamino} ethoxy]-4,6-bis (trichloro methyl)-s-triazine, 2-[2-{N,N-diallyl amino} ethoxy]-4,6-bis (trichloro methyl)-s-triazine and the like. Among them, 2,4,6-tris (trichloro methyl)-s-triazine is preferable.

Any iodonium salt-based compound can be used as long as it is known. For the specific examples, the structural formula of the iodonium salt-based compound can be represented by the following formula (1).

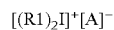

$$[(R1)_2I]^+[A]^-$$ [Formula (1)]

(In the formula, $[(R1)_2I]^+$ is a cation part, $[A]^-$ is an anion part, R1 shown in the formula (1) represents an organic group bonded to I, and R1s may be the same or different. R1 represents, for example, an aryl group having 6 to 30 carbon atoms, a heterocyclic group having 4 to 30 carbon atoms, an alkyl group having 1 to 30 carbon atoms, an alkenyl group having 2 to 30 carbon atoms, or an alkynyl group having 2 to 30 carbon atoms, which may have at least one substituted group selected from the group consisting of groups such as alkyl, hydroxy, alkoxy, alkylcarbonyl, arylcarbonyl, alkoxycarbonyl, aryloxycarbonyl, arylthiocarbonyl, acyloxy, arylthio, alkylthio, aryl, heterocycle, aryloxy, alkylsulfinyl, arylsulfinyl, alkylsulfonyl, arylsulfonyl, alkyleneoxy, amino, cyano, nitro groups and halogens.)

In the above, examples of the aryl group having 6 to 30 carbon atoms include a monocyclic aryl group such as a phenyl group and a condensed polycyclic aryl group such as a naphthyl, anthrasenyl, phenanthrenyl, pyrenyl, chrysenyl, naphthacenyl, benzanthrasenyl, anthraquinolyl, fluorenyl, naphthoquinone and anthraquinone.

Examples of the heterocyclic group having 4 to 30 carbon atoms include cyclic groups containing 1 to 3 heteroatoms such as oxygen, nitrogen, and sulfur, which may be the same or different. Specific examples include a monocyclic heterocyclic group such as thienyl, furanyl, pyranyl, pyrrolyl, oxazolyl, thiazolyl, pyridyl, pyrimidyl and pyrazinyl, and a condensed polycyclic heterocyclic group such as indolyl, benzofuranyl, isobenzofuranyl, benzothienyl, isobenzothienyl, quinolyl, isoquinolyl, quinoxalinyl, quinazolinyl, carbazolyl, acridinyl, phenothiazinyl, phenazinyl, xanthenyl, thianthrenyl, phenoxazinyl, phenoxathiinyl, chromanyl, isochromanyl, dibenzothienyl, xanthonyl, thioxanthonyl and dibenzofuran.

Specific examples of alkyl groups having 1 to 30 carbon atoms include a linear alkyl group such as methyl, ethyl, propyl, butyl, hexadecyl and octadecyl, a branched alkyl group such as isopropyl, isobutyl, sec-butyl, tert-butyl, isopentyl, neopentyl, tert-pentyl, isohexyl and a cycloalkyl groups such as cyclopropyl, cyclobutyl, cyclopentyl and cyclohexyl.

In addition, specific examples of the alkenyl group having 2 to 30 carbon atoms include a linear chain or branched group such as vinyl, allyl, 1-propenyl, isopropenyl, 1-butenyl, 2-butenyl, 3-butenyl and 1-methyl-1-propenyl.

Further, specific examples of the alkynyl group having 2 to 30 carbon atoms include a linear chain or branched group such as ethynyl, 1-propynyl, 2-propynyl, 1-butynyl, 2-butynyl, 3-butynyl, 1-methyl-1-propynyl and 1-methyl-2-propynyl.

The above-described aryl group having 6 to 30 carbon atoms, heterocyclic group having 4 to 30 carbon atoms, alkyl group having 1 to 30 carbon atoms, alkenyl group having 2 to 30 carbon atoms and alkynyl group having 2 to 30 carbon atoms may have at least one substituted group. Specific examples of the substituted group include a linear alkyl group having 1 to 18 carbon atoms such as methyl, ethyl, propyl, butyl and octadecyl; a branched alkyl group having 1 to 18 carbon atoms such as isopropyl, isobutyl, sec-butyl and tert-butyl; a cycloalkyl group having 3 to 18 carbon atoms such as cyclopropyl, cyclobutyl, cyclopentyl and cyclohexyl; a hydroxy group; a linear chain or branched alkoxy group having 1 to 18 carbon atoms such as methoxy ethoxy propoxy isopropoxy, butoxy, isobutoxy, sec-butoxy, tert-butoxy and dodecyloxy; a linear chain or branched alkylcarbonyl group having 2 to 18 carbon atoms such as acetyl, propionyl, butanoyl, 2-methylpropionyl, heptanoyl, 2-methylbutanoyl, 3-methylbutanoyl and octanoyl; an arylcarbonyl group having 7 to 11 carbon atoms such as benzoyl and naphthoyl; a linear chain or branched alkoxycarbonyl group having 2 to 19 carbon atoms such as methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl; an aryloxycarbonyl group having 7 to 11 carbon atoms such as phenoxycarbonyl and naphthoxycarbonyl; an arylthiocarbonyl group having 7 to 11 carbon atoms such as phenylthiocarbonyl and naphthoxythiocarbonyl; a linear chain or branched acyloxy group having 2 to 19 carbon atoms such as acetoxy, ethylcarbonyloxy, propylcarbonyloxy, isobutylcarbonyloxy, sec-butylcarbonyloxy, tert-butylcarbonyloxy and octadecylcarbonyloxy; an arylthio group having 6 to 20 carbon atoms such as phenylthio, biphenylthio, methylphenylthio, chlorophenylthio, bromophenylthio, fluorophenylthio, hydroxyphenylthio, methoxyphenylthio, naphthylthio, 4-[4-(phenylthio) benzoyl]phenylthio, 4-[4-(phenylthio) phenoxy] phenylthio, 4-[4-(phenylthio) phenyl] phenylthio, 4-(phenylthio) phenylthio, 4-benzoyl phenylthio, 4-benzoyl-chlorophenylthio, 4-benzoyl-methylthio phenylthio, 4-(methylthiobenzoyl) phenylthio and 4-(p-tert-butylbenzoyl) phenylthio; a linear chain or branched alkylthio group having 1 to 18 carbon atoms such as methylthio, ethylthio, propylthio, tert-butylthio, neopentylthio and dodecylthio; an aryl group having 6 to 10 carbon atoms such as phenyl, tolyl, dimethylphenyl and naphthyl; a heterocycle group having 4 to 20 carbon atoms such as thienyl, furanyl, pyranyl, xanthenyl, chromanyl, isochromanyl, xanthonyl, thioxanthonyl and dibenzofuranyl; an aryloxy group having 6 to 10 carbon atoms such as phenoxy and naphthyloxy; a linear chain or branched alkylsulfinyl group having 1 to 18 carbon atoms such as methylsulfinyl, ethylsulfinyl, propylsulfinyl, tert-pentylsulfinyl and octylsulfinyl; an arylsulfinyl group having 6 to 10 carbon atoms such as phenylsulfinyl, tolylsulfinyl and naphthylsulfinyl; a linear chain or branched alkylsulfonyl group having 1 to 18 carbon atoms such as methylsulfonyl, ethylsulfonyl, propylsulfonyl, isopropylsulfonyl, butylsulfonyl and octylsulfonyl; an arylsulfonyl group having 6 to 10 carbon atoms such as phenylsulfonyl, tolylsulfonyl (tosyl), naphthylsulfonyl; an alkyleneoxy groups; a cyano groups; a nitro groups; and halogens such as fluorine, chlorine, bromine and iodine.

Among the iodonium salt-based compounds, the aryl iodonium salt is preferable because of having high stability. Further, it is preferable that the aryl group has a substituent in order to improve the solubility to the photopolymerization composition. Specifically, a linear alkyl group such as methyl, propyl, octyl, decyl, undecyl, dodecyl and tridecyl, a branched alkyl group such as isopropyl, isobutyl, sec-butyl, tert-butyl, isopentyl, neopentyl, tert-pentyl and isohexyl, a functional group in which one or more of H of these is substituted with F, a perfluoroalkyl group and halogen is suitable as the substituent.

The structure of an anion portion of the iodonium salt-based compound is not particularly limited, and examples include those having atoms such as halogen, P, S, B, Al and Ga. From the viewpoint of safety, anions having As or Sb can be used, but they are not preferable in dental applications. Further, the anion preferably has an organic group such as an alkyl group and/or an alkoxy group and/or an aryl group, and further, most preferably has an organic group such as an alkyl group and/or an alkoxy group and/or an aryl group, in which at least one H is substituted with F. Since the iodonium salt-based compound having such an anion has high solubility in the photocurable composition, it is expected to preventing precipitation during low-temperature storage or long-term storage and to shorten the time for preparing due to dissolving in the composition in a short time. Further, an iodonium salt-based compound of an anion having an organic group such as an alkyl group and/or an alkoxy group and/or an aryl group, in which at least one H is substituted with F can be expected to have higher solubility. When the photoacid generator is precipitated, there is a case that it may cause a decrease in light color stability and a decrease in flexural strength, and therefore it is not preferable. As the anion having an organic group such as an alkyl group and/or an alkoxy group and/or an aryl group, in which at least one H is substituted with F, an anion having any atom can be used. However, from the viewpoint of versatility and safety, those having one or more of P, S, B, Al and Ga are preferable.

Examples of the anion having no alkyl group and/or alkoxy group and/or aryl group include halogens such as chloride and bromide, perhalonic acids such as perchloric acid, aromatic sulfonic acids such as p-toluenesulfonate, camphorsulfonnic acids, nitrates, acetates, chloroacetates, carboxylates, phenolates, tetrafluoroborates, hexafluorophosphates, hexafluoroantimonates, hexafluoroarsenates and the like. Among these, p-toluenesulfonate, camphorsulfonic acid and carboxylate are preferably used.

Since the anionic part of $[A]^-$ of the iodonium salt-based compound of the formula (1) improves the solubility to the photopolymerization composition, it is preferable that the anion has an organic group such as alkyl group and/or alkoxy group and/or aryl group, in which at least one H is substituted with F. Specifically, the number of carbon atoms of the alkyl group in the anion part of $[A]^-$ of the iodonium salt-based compound of the formula (1) is 1 to 8, and preferably 1 to 4. Specific examples include a linear alkyl group such as methyl, ethyl, propyl, butyl, pentyl and octyl, a branched alkyl group such as isopropyl, isobutyl, sec-butyl and tert-butyl, and a cycloalkyl group such as cyclopropyl, cyclobutyl, cyclopentyl and cyclohexyl. The ratio (F/H) of the number of hydrogen atoms to fluorine atoms in the alkyl group is 4 or more, and the ratio (F/H) of the number of hydrogen atoms to fluorine atoms in the alkyl group is preferably 9 or more. More preferably, all hydrogen atoms of the hydrocarbon are substituted with fluorine. An iodonium salt consisting of an anion having an alkyl group having a different ratio of a hydrogen atom and a fluorine atom may be compounded in the photocurable composition.

Further, specific examples of the alkyl group include a linear chain or branched perfluoroalkyl group such as $CF_3$, $CF_3CF_2$, $(CF_3)_2CF$, $CF_3CF_2CF_2$, $CF_3CF_2CF_2CF_2$, $(CF_3)_2CFCF_2$, $CF_3CF_2(CF_3)CF$ and $(CF_3)_3C$.

The number of carbon atoms of the alkyl group in the anion part of $[A]^-$ of the iodonium salt-based compound of the formula (1) is 1 to 8, and preferably 1 to 4. Specific examples include a linear alkoxy group such as methoxy, ethoxy, propoxy, butoxy, pentoxy and octoxy, and a branched alkoxy group such as isopropoxy, isobutoxy, sec-butoxy and tert-butoxy. The ratio (F/H) of the number of hydrogen atoms to fluorine atoms in the alkyl group is 4 or more, and the ratio (F/H) of the number of hydrogen atoms to fluorine atoms in the alkyl group is preferably 9 or more. More preferably, all hydrogen atoms of the hydrocarbon are substituted with fluorine. An iodonium salt consisting of an anion having an alkoxy group having a different ratio of a hydrogen atom and a fluorine atom may be compounded in the photocurable composition.

Further, specific examples of the alkoxy group include a linear or branched perfluoroalkoxy group such as $CF_3O$, $CF_3CF_2O$, $CF_3CF_2CF_2O$, $(CF_3)_2CFO$, $CF_3CF_2CF_2CF_2O$, $(CF_3)_2CFCF_2O$, $CF_3CF_2(CF_3)CFO$, $CF_3CF_2CF_2CF_2CF_{20}$ and $CF_3CF_2CF_2CF_2CF_2CF_2CF_2CF_2O$.

The phenyl group in the anion part of $[A]^-$ of the iodonium salt compound of the formula (1) may be a phenyl group, in which at least one H is substituted with fluorine atom, an alkyl group and/or an alkoxy group substituted with fluorine atom. The alkyl group and/or alkoxy group substituted with fluorine atom are preferably those described above. Specific examples of particularly preferable phenyl group include perfluorophenyl group such as pentafluorophenyl group ($C_6F_5$), trifluorophenyl group ($C_6H_2F_3$), tetrafluorophenyl group ($C_6HF_4$), trifluoromethylphenyl group ($CF_3C_6H_4$), bis (trifluoromethyl) phenyl group (($CF_3$)$_2C_6H_3$), pentafluoroethyl phenyl group ($CF_3CF_2C_6H_4$), bis (pentafluoroethyl) phenyl group (($CF_3CF_2$)$_2C_6H_3$), trifluoromethyl fluorophenyl group ($CF_3C_6H_3F$), bistrifluoromethyl fluorophenyl group (($CF_3$)$_2C_6H_2F$), pentafluoroethyl fluorophenyl group ($CF_3CF_2C_6H_3F$), bispentafluoroethyl fluorophenyl group ($CF_3CF_2$)$_2C_6H_2F$ and the like. An iodonium salt consisting of an anion having a phenyl group having a different ratio of a hydrogen atom and a fluorine atom may be compounded in the photocurable composition.

As specific examples of the anion portion of $[A]^-$ of the iodonium salt compound of the formula (1), examples of the anion having P include $[(CF_3CF_2)_3PF_3]^-$, $[(CF_3CF_2CF_2)_3PF_3]^-$, $[((CF_3)_2CF)_2PF_4]^-$, $[((CF_3)_2CF)_3PF_3]^-$, $[((CF_3)_2CF)_4PF_2]^-$, $[((CF_3)_2CFCF_2)_2PF_4]^-$, $[((CF_3)_2CFCF_2)_3PF_3]^-$ and the like. Examples of the anion having S include $[(CF_3SO_2)_3C]^-$, $[(CF_3CF_2SO_2)_3C]^-$, $[(CF_3CF_2CF_2SO_2)_3C]^-$, $[(CF_3CF_2CF_2CF_2SO_2)_3C]^-$, $[CF_3CF_2CF_2CF_2SO_3]^-$, $[CF_3CF_2CF_2SO_3]^-$, $[(CF_3SO_2)_3C]^-$, $[(SO_2CF_3)_3N]^-$, $[(SO_2CF_2CF_3)_2N]^-$, $[((CF_3)C_6H_4)SO_3]^-$, $[SO_3(CF_2CF_2CF_2CF_2)SO_3]^{2-}$ and the like. Examples of the anion having B include $[B(C_6F_5)_4]^-$, $[(C_6H_5)B(C_6F_5)_3]^-$, $[(C_6H_5)B((CF_3)_2C_6H_3)_3]^-$ and the like. Examples of an anion having Ga include $[((CF_3)_4Ga)]^-$, $[Ga\ (C_6F_5)_4]^-$ and the like. Examples of anions having Al include $[((CF_3)_3CO)\ 4Al]^-$, $[((CF_3CF_2)_3CO)_4Al]^-$.

The dental photocurable composition of the present disclosure may contain only an aryliodonium salt as the (C) photoacid generator. The dental photocurable composition of the present disclosure may comprise only an aryl iodonium salt which is a salt of an anion having an organic group and one or more atoms of P, B, Al, S and Ga, and an aryl iodonium cation as the (C) photoacid generator. The dental photocurable composition of the present disclosure may comprise only an aryl iodonium salt which is a salt of an anion having an organic group in which at least one H may be substituted with F and one or more atoms of P, B, Al, S and Ga, and an aryl iodonium cation.

The dental photocurable composition of the present disclosure contains 0.5 parts by mass or more of the (C) photoacid generator with respect to 100 parts by mass of the total amount of the (A) polymerizable monomer. The compounding amount is preferably 0.5 to 10 parts by mass, and more preferably 1 to 5 parts by mass. When the compounding amount of the photoacid generator is less than 0.5 parts by mass, the polymerization promoting ability is poor and the curing becomes insufficient. When the compounding amount is more than 10 parts by mass, although it has sufficient curability, the environmental light stability is shortened, and discoloration such as browning or yellowing of the cured body may increase, and therefore it is not preferable.

The photoacid generator that can be used in the dental photocurable composition of the present disclosure is not limited to the photoacid generator described in the specific example, and two or more types can be used in combination.

[(D) Photopolymerization Accelerator]

The (D) photopolymerization accelerator which is used for the dental photocurable composition of the present disclosure is not particularly limited as long as it has polymerization promoting ability, and any known photopolymerization accelerator commonly used in the dental field may be used without any limitation. As the photopolymerization accelerator, a primary to tertiary amine compound such as an aromatic amine compound and an aliphatic amine compound, an organic metal compound, a phosphine compound and the like can be used. Among these, a tertiary aliphatic amine compound and an organic metal compound are preferable because of having good light color stability.

Aromatic amine compound refers to a compound in which one or more H of ammonia ($NH_3$) is replaced with an aromatic ring. Aromatic amine compound in which one H of $NH_3$ is substituted with an aromatic ring is classified into an aromatic primary amine compound, aromatic amine compound in which one H of $NH_3$ is substituted with an aromatic ring and one H of remaining two H is substituted with an aromatic ring or an alkyl group is classified into an aromatic secondary amine compound, and aromatic amine compound in which one H of $NH_3$ is substituted with an aromatic ring and remaining two H are substituted with an aromatic ring or an alkyl group is classified into an aromatic tertiary amine compound.

Specific examples of the aromatic primary amine compound include aniline. Specific examples of the aromatic secondary amine compound include N-protected amino acid (ester) such as N-phenyl benzylamine, N-benzyl-p-anisidine, N-benzyl-o-phenetidine, N-phenylglycine ethyl and N-phenylglycine. Specific examples of the aromatic tertiary amine compound include N,N-dimethylaniline, N,N-diethylaniline, N,N-di-n-butylaniline, N,N-dibenzylaniline, p-N,N-dimethyl-toluidine, m-N,N-dimethyl-toluidine, p-N,N-diethyl-toluidine, p-bromo-N,N-dimethylaniline, m-chloro-N,N-dimethylaniline, p-dimethylamino benzaldehyde, p-dimethylamino acetophenone, p-dimethylamino benzoic acid, p-dimethylamino benzoic acid ethyl ester, p-dimethylamino benzoic acid isoamyl estel, p-dimethylamino benzoic acid 2-butoxyethyl, p-dimethylamino benzoic acid 2-ethylhexyl, p-dimethylamino benzoic acid amino ester, N,N-dimethyl anthranic acid methyl ester, N,N-dihydroxyethyl aniline, N,N-diisopropanol aniline, p-N,N-dihydroxyethyl-toluidine, p-N,N-diisopropanol-toluidine, p-dimethylamino phenyl alcohol, p-dimethylamino styrene, N,N-dimethyl-3,5-xylidine, 4-dimethylamino pyridine, N,N-dimethyl-α-naphthylamine, N,N-dimethyl-8-naphthylamine and the like.

Specific examples of the above organic metal compound include an orgic metal compound containing scandium (Sc), titanium (Ti), vanadium (V), manganese (Mn), iron (Fe), cobalt (Co), nickel (Ni), copper (Cu), tin (Sn), zinc (Zn)

an/or zirconia (Zr), and an organic metal compound containing tin (Sn), vanadium (V) and/or copper (Cu) is preferable. Specific examples of the organic metal compound containing tin (Sn) include dibutyl-tin-diacetate, dibutyl-tin-dimaleate, dioctyl-tin-dimaleate, dioctyl-tin-dilaurate, dibutyl-tin-dilaurate, dioctyl-tin-diversate, dioctyl-tin-S,S'-bis-isooctyl mercapto acetate, tetramethyl-1,3-diacetoxy distanoxane and the like. Specific examples of the organic metal compound containing vanadyl (V) include acetylacetone vanadium, divanadium tetraoxide, vanadyl acetylacetonate, vanadyl stearate oxide, vanadyl oxalate, vanadyl sulphate, oxobis (1-phenyl-1,3-butandionate) vanadium, bis (maltlate) oxovanadium, vanadium pentoxide and sodium metavanadate. Specific examples of the organic metal compound containing copper (Cu) include copper acetylacetone, copper naphthenate, copper octylate, copper stearate and copper acetate.

The phosphine compound refers to a compound which is trisubstituted on P atom with organic groups, and the aromatic phosphine compound refers to a compound which is substituted on P atom with a phenyl group which may have one or more substituents. Specific examples of the phosphine compound include trimethylphosphine, tributylphosphine, trihexylphosphine, tri-n-octylphosphine, tricyclohexylphosphine, tri (2-thienyl) phosphine, diphenylpropyl phosphine, di-tert-butyl (3-methyl-2-butenyl) phosphine, methyldiphenyl phosphine, triphenyl phosphine, 2-(diphenylphosphino) styrene, 3-(diphenylphosphino) styrene, 4-(diphenylphosphino) styrene, allyldiphenyl phosphine, 2-(diphenylphosphino) benzaldehyde, 3-(diphenylphosphino) benzaldehyde, 4-(diphenylphosphino) benzaldehyde, 2-(phenylphosphine) benzoic acid, 3-(phenylphosphino) benzoic acid, 4-(phenylphosphino) benzoic acid, tris (2-methoxyphenyl) phosphine, tris (3-methoxyphenyl) phosphine, tris (4-methoxyphenyl) phosphine, 2-(diphenylphosphino) biphenyl, tris (4-fluorophenyl) phosphine, tri (o-trill) phosphine, tri (m-trill) phosphine, tri (p-trill) phosphine, 2-(dimethylamino) phenyldiphenyl phosphine, 3-(dimethylamino) phenyldiphenyl phosphine, 4-(dimethylamino) phenyldiphenyl phosphine, 2,2'-bis (diphenylphosphino) biphenyl, bis [2-(diphenylphosphino) phenyl] ether and the like. Among them, triphenylphosphine, 4-(phenylphosphino) benzoic acid, tri (o-tolyl) phosphine, tri (m-tolyl) phosphine and tri (p-tolyl) phosphine are preferable.

Aliphatic amine compounds refer to compounds in which one or more H of ammonia ($NH_3$) are substituted with alkyl group. As for the alkyl group, $CH_3$— and —$CH_2$— are classified as a primary alkyl group, the one in which one H of —$CH_2$— is substituted with a substituent is classified as a secondary alkyl group, and the one in which two H of —$CH_2$— are substituted with substituents is classified as a tertiary alkyl group. Aliphatic amine in which one H of $NH_3$ is substituted with an alkyl group is classified into an aliphatic primary amine compound, aliphatic amine compound in which two H of $NH_3$ are substituted with an alkyl group is classified into an aliphatic secondary amine compound, and aliphatic amine compound in which three H of $NH_3$ are substituted with an alkyl group is classified into an aliphatic tertiary amine compound.

Specific examples of the aliphatic primary amine compound include amino acid or amino acid ester such as benzhydrylamine, triphenylmethylamine and glycine. Specific examples of the aliphatic secondary amine compound include dibenzylamine, N-benzyl-1-phenylethylamine, bis (1-phenylethyl) amine, bis (4-cyanobenzyl) amine, N-benzyl protected amino acid and N-benzyl protected amino acid ester. Specific examples of the aliphatic tertiary amine compound include tributylamine, tripropylamine, triethylamine, N,N-dimethyl hexylamine, N,N-dimethyl dodecylamine, N,N-dimethyl stearylamine, N-[3-(dimethylamino) propyl] acrylamide, N,N-dimethyl formamide dimethylacetal, N,N-dimethylacetamide dimethylacetal, N,N-dimethylformamide diethylacetal, N,N-dimethylformamide dipropylacetal, N,N-dimethylformamide di-tert-butylacetal, 1-(2-hydroxyethyl) ethyleneimine, N,N-dimethyl ethanolamine, N,N-dimethyl isopropanolamine, N,N-diisopropyl ethanolamine, N-methyl diethanolamine, N-ethyl diethanolamine, N-ethyl diethanolamine, N-butyl diethanolamine, N-lauryl diethanolamine, N-stearyl diethanolamine, triethanolamine, triisopropanolamine, tribenzylamine, dibenzylglycine ethylester, N'-(2-hydroxyethyl)-N,N,N'-trimethylethylene diamine, 2-(dimethylamino)-2-methyl-1-propanol, N,N-dimethyl-2,3-dihydroxy propylamine, N,N-diethylethanolamine, 1-methyl-3-pyrrolidinol, 1-(2-hydroxyethyl) pyrrolidine, 1-isopropyl-3-pyrrolidinol, 1-piperidin ethanol, 2-[2-(dimethylamino) ethoxy] ethanol, N,N-dimethylglycine, N,N-dimethylglycine methyl, N,N-diethylglycine methyl, N,N-dimethylglycine ethyl, N,N-diethylglycine sodium, 2-(dimethylamino) ethylacetate, N-methylimimino diacetic acid, N,N-dimethylamino ethylacrylate, N,N-diethylamino ethylmethacrylate, N,N-diisopropylamino ethyl methacrylate, N,N-dibutylamino ethylmethacrylate, N,N-dibenzylamino ethylmethacrylate, 3-dimethylamino propionitrile, tris (2-cyanoethyl) amine, N,N-dimethyl allylamine, N,N-diethyl allylamine and triallylamine.

As the (D) photopolymerization accelerator, it is particularly preferable to use an aliphatic tertiary amine compound. Since the aromatic amine compound is inferior in light color stability, these is a case in which the color tone may change over time in the case of using for a prosthetic device, a restoration material or an adhesive material in a place easily exposed with light such as an anterior tooth, and therefore it is not preferable. It can be expected to suppress discoloration over time due to light by using in combination with an ultraviolet absorber. However, since the ultraviolet absorber is usually used as an additive, it cannot be expected to improve the mechanical characteristics by compounding, and in addition, there is a case that the yellowness of the dental photocurable composition before curing may increase. Therefore, a large amount of compounding is not preferable. From these facts, it is preferable to use an aliphatic tertiary amine compound. Further, depending on the composition of the dental photocurable composition, high storage stability and high mechanical strength can be expected in the case of containing an aliphatic primary amine compound and an aliphatic secondary amine compound, and therefore any known compound can be used without any limitation.

Further, among the aliphatic tertiary amine compounds, (D-1) aliphatic tertiary amine compound which is not an aliphatic tertiary amine compound having two or more primary hydroxy groups in the molecule, that is, (D-1) aliphatic tertiary amine compound not having two or more primary hydroxy groups in the molecule is preferable, and an aliphatic tertiary amine compound having no primary hydroxy group in the molecule is more preferable. Specific examples of the aliphatic tertiary amine compound having two or more primary hydroxy groups in the molecule include triethanolamine and methyldiethanolamine. Specific examples of the (D-1) aliphatic tertiary amine compound not having two or more primary hydroxy groups include N,N-dimethyl ethanolamine, N,N-diethyl ethanolamine, N,N-dibenzyl ethanolamine. When a large amount of a low boiling point compound such as N,N-dimethyl ethanolamine and N,N-diethyl ethanolamine are compounded, an odor peculiar to amine is generated. Therefore, among the above-described specific examples, N,N-dibenzyl ethanolamine is preferable. Specific examples of the aliphatic tertiary amine compound having no primary hydroxy group in the molecule include tribenzylamine, N,N-dibenzylglycine ethyl ester, dimethylaminoethyl methacrylate, diethylaminoethyl methacrylate and the like. An amine compound having a primary hydroxy group may cause discoloration when the cured product of the dental photocurable composition is stored for a long period of time. There is a tendency that the discoloration increases as the number of primary hydroxy groups in the molecule increases, and the tendency is particularly remarkable when two or more primary hydroxy groups are present in the molecule. Discoloration in the case of storing a cured product for a long period of time can be confirmed in a short period of time by storing it under a condition of high temperature water. When the discoloration under the condition of high temperature water is small, that is, when the thermal color stability is high, the discoloration after long-term use of the cured product of the dental photocurable composition is small.

The dental photocurable composition of the present disclosure may contain only an aliphatic tertiary amine compound as the (D) photopolymerization accelerator. The dental photocurable composition of the present disclosure may contain only (D1) aliphatic tertiary amine compound not having two or more primary hydroxy groups as the (D) photopolymerization accelerator. The dental photocurable composition of the present disclosure may contain only an aliphatic tertiary amine compound having no primary hydroxy group in the molecule as the (D) photopolymerization accelerator.

The compounding amount of the (D) photopolymerization accelerator is preferably 0.1 to 20 parts by mass, more preferably 0.1 to 10 parts by mass, most preferably 0.5 to 10 parts by mass, with respect to 100 parts by mass of the total amount of the (A) polymerizable monomer. When the compounding amount is less than 0.1 parts by mass, there is a case where the mechanical strength is insufficient. When the compounding amount is more than 20 parts by mass, although it has sufficient curability, the environmental light stability is shortened, and discoloration such as browning or yellowing of the cured body may increase, and therefore it is not preferable.

There is no problem even if these (B) photosensitizers, (C) photoacid generators and (D) photopolymerization accelerators, which are polymerization initiators, are subjected to a secondary treatment such as finely pulverization, adsorption on a carrier and encapsulation in a microcapsule, if necessary. Furthermore, these photo polymerization initiators can be used not only singly but also in combinations of two or more, regardless of the polymerization manner or the polymerization method.

[(E) Filler]

As the (E) filler used in the present disclosure, a known filler commonly used can be used without any limitation.

The type of the (E) filler is not limited as long as it is a known filler, and a filler suitable for the application can be compounded, and it is preferable that a filler such as an inorganic filler, an organic filler and an organic-inorganic composite filler is compounded. These fillers can be used not only singly but also in combinations of a plurality thereof regardless of the types of the fillers.

As the above described inorganic filler, the chemical composition is not particularly limited, but specific examples include silicon dioxide, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, strontium calcium fluoroaluminosilicate glass and the like. Particularly, barium fluoroaluminosilicate glass, strontium fluoroaluminosilicate glass, fluoroaluminosilicate glass and the like, which are used in dental glass ionomer cement, resin reinforced glass ionomer cement and resin cement and the like, can also be suitably used. The fluoroaluminosilicate glass as used herein has a basic structure of silicon oxide and aluminum oxide and contains an alkali metal for introducing non-crosslinked oxygen. The fluoroaluminosilicate glass further has an alkaline earth metal including strontium and fluorine as modified/coordinated ions. The fluoroaluminosilicate glass may be also a composition in which a lanthanoid series element is incorporated into the skeleton in order to impart further radiopacity. This lanthanoid series element also participates in the composition as a modified/coordinated ion.

Specific examples of the organic filler include polymers such as polymethyl methacrylate, polyethyl methacrylate, methyl methacrylate-ethyl methacrylate copolymer, ethyl methacrylate-butyl methacrylate copolymer, methyl methacrylate-trimethylolpropane methacrylate copolymer, polyvinylchloride, polystyrene, chlorinated polyethylene, nylon, polysulfone, polyethersulfone and polycarbonate.

In addition, examples of the organic/inorganic composite filler include one obtained by covering the surface of a filler with a polymerizable monomer by polymerization, one obtained by mixing a filler and a polymerization monomer and polymerizing the monomer, and thereafter grinding the resultant to a proper particle size, or one obtained by dispersing a filler in a polymerizable monomer in advance for emulsion polymerization or suspension polymerization, but are not limited thereto at all.

The above described (E) filler can be treated with a surface treatment material represented by a silane coupling material in order to improve the affinity to the polymerizable monomer, the dispersibility in the polymerizable monomer, and the mechanical strength and water resistance of the cured product. The surface treatment material and the surface treatment method are not particularly limited, and known methods can be adopted without limitation. As a silane coupling material used for surface treatment of the filler, methyltrimethoxysilane, methyltriethoxysilane, methyltrichlorosilane, dimethyldichlorosilane, trimethylchlorosilane, vinyltrichlorosilane, vinyltriethoxysilane, vinyltris (2-methoxyethoxy) silane, 3-methacryloyloxypropyl trimethoxysilane, 3-chloropropyl trimethoxysilane, 3-glycidoxypropyl trimethoxysilane, 3-(meth) acryloxypropyl trimethoxysilane, 8-(meth) acryloxyoctyl trimethoxysilane, 11-(meth) acryloxiundecyl trimethoxysilane, hexamethyldisilazane and the like are preferable. In addition to the silane coupling material, surface treatment of the filler can be performed by a method using a titanate coupling material or an aluminate coupling material. The treatment amount of the surface treatment material in the filler is preferably 0.01 to 30 parts by mass, more preferably 0.5 to 20 parts by mass with respect to 100 parts by mass of the filler before treatment.

The shape of the filler is not particularly limited, and any shape of the filler such as an amorphous, a spherical shape, a needle shape, a plate shape, a crushed shape or a scale shape can be used. The average particle diameter of the filler is preferably 0.01 µm to 50 µm, more preferably 0.01 µm to 30 µm, still more preferably 0.05 µm to 20 µm, and more preferably 0.05 µm to 10 µm.

The dental photocurable composition of the present disclosure contains 100 parts by mass or more of the (E) filler with respect to 100 parts by mass of the total amount of the (A) polymerizable monomer. When the compounding amount of the (E) filler is less than 100 parts by mass, the proportion of the (B) α-diketone compound in the dental photocurable composition is large as compared with the case where the compounding amount of the (E) filler is 100 parts by mass or more, and therefore there is a case that the change in color difference between before curing and after curing may be large. When the dental photocurable composition is one pack type dental photocurable composition, the compounding amount of the (E) filler is preferably 150 parts by mass or more and 1000 parts by mass or less. When the compounding amount is more than 1000 parts by mass, the paste property of the composition becomes hard and there is a case that it is difficult to handle. However, depending on the type of the filler and the surface treatment condition of the filler, there is a case where 1000 parts by mass or more is contained. For example, it refers to the case where the filler has a high specific gravity, the amount of the surface treatment agent to the filler is large, and the case where a surface treatment agent having a good affinity with the polymerizable monomer is used. When the dental photocurable composition is two packs type, the compounding amount of the (E) filler is preferably 200 parts by mass or more and 800 parts by mass or less with respect to 200 parts by mass of total of the (A) polymerizable monomer contained in the first matrix constituting the first paste and the second matrix constituting the second paste.

The dental photocurable composition of the present disclosure may contain a chemical polymerization initiator. Specific examples of an organic peroxide as chemical polymerization initiator include diacyl peroxides, peroxy esters, dialkyl peroxides, peroxy ketals, ketone peroxides, peroxy dicarbonates, and hydro peroxides. Specific examples of diacyl peroxides include acetyl peroxide, isobutyryl peroxide, benzoyl peroxide, decanoyyl peroxide, 3,5,5-trimethylhexanoyl peroxide, 2,4-dichlorobenzoyl peroxide, and lauroyl peroxide and the like. Specific examples of peroxyesters include α-cumylperoxy neodecanoate, t-butylperoxy neodecanoate, t-butylperoxy pivalate, 2,2,4-trimethylpentyl peroxy-2-ethyl hexanoate, t-amylperoxy-2-ethylhexanoate, t-butylperoxy-2-ethylhexanoate, di-t-butylperoxy isophthalate, di-t-butylperoxy hexahydro terephthalate, t-butylperoxy-3,3,5-trimethyl hexanoate, t-butylperoxy acetate, t-butylperoxy benzoate and t-butylperoxy maleric acid. Specific examples of dialkyl peroxides include di-t-butyl peroxide, dicumyl peroxide, t-butylcumyl peroxide, 2,5-dimethyl-2,5-di (t-butylperoxy) hexane, 1,3-bis (t-butylperoxy isopropyl) benzene, 2,5-dimethyl-2,5-di (t-butylperoxy)-3-hexyne and the like. Specific examples of peroxyketals include 1,1-di (t-butylperoxy) cyclohexane, 2,2-di (t-butylperoxy) butane, and n-butyl-4,4-(t-butylperoxy) parerate, 1,1-di (t-amylperoxy) cyclohexane and the like. Specific examples of ketone peroxides include methyl ethyl ketone peroxide, methyl isobutyl ketone peroxide, methyl cyclohexanone peroxide, cyclohexanone peroxide and the like. Specific examples of peroxydicarbonates include di-3-methoxyperoxy dicarbonate, di-2-ethylhexylperoxy dicarbonate, bis (4-t-butylcyclohexyl) peroxy dicarbonate, diisopropylperoxy dicarbonate, di-n-propylperoxy dicarbonate, di-2-ethoxyethylperoxy dicarbonate, diallylperoxy dicarbonate and the like. Specific examples of hydroperoxides include 2,5-dimethyl hexane-2,5-dihydroperoxide, diisopropylbenzene hydroperoxide, cumene hydroperoxide, t-butyl hydroperoxide and 1,1,3,3-tetramethyl butylhydroperoxide.

As the organic peroxide, the above-mentioned organic peroxides may be used alone, or two or more kinds of organic peroxides may be used in combination. Among these organic peroxides, benzoyl peroxide and cumene hydroperoxide are preferable from the viewpoint of curability. The compounding amount of the organic peroxide as a chemical polymerization initiator is preferably set to 0.1 to 5 parts by mass, more preferably set to 0.3 to 3 parts by mass with respect to 100 parts by mass of the total amount of the (A) polymerizable monomer from the viewpoint of improving the curability. When the compounding amount of the organic peroxide is more than 5 parts by mass, it may be difficult to ensure sufficient operation time. On the other hand, when the compounding amount of the organic peroxide is less than 0.1 parts by mass, there is a case in which mechanical strength may be insufficient.

In the dental photocurable composition of the present disclosure, in order to improve the curability, a chemical polymerization accelerator may further be compounded. Examples of chemical polymerization accelerators include a transition metal compound of the group 4 in the periodic table, a thiourea derivative an aliphatic amine, an aromatic amine, a sulfinic acid and a salt thereof, a borate compound, a sulfur-containing reductive inorganic compound, a nitrogen-containing reductive inorganic compound, a barbituric acid derivative, a triazine compound, a halogen compound and the like. The compounding amount of the chemical polymerization accelerator is preferably 0.01 to 5 parts by mass, more preferably 0.1 to 3 parts by mass, with respect to 100 parts by mass of the total amount of (A) polymerizable monomer.

The transition metal compound of the period 4 in the periodic table as a chemical polymerization accelerator refers to a metal compound of groups 3 to 12 of the period 4 in the periodic table, and specifically, each metal compound of scandium (Sc), titanium (Ti), vanadium (V), manganese (Mn), iron (Fe), cobalt (Co), nickel (Ni), copper (Cu), and zinc (Zn) can be used without any limitation. Although each of the above transition metal element may have a multiple valences, they can be added to the dental photocurable composition of the present disclosure as long as the valence is stable. Examples include Sc (trivalent), Ti (tetravalent), V (trivalent, tetravalent or pentavalent), Cr (divalent, trivalent or hexavalent), Mn (divalent to heptavalent), Fe (divalent or trivalent), Co (divalent or trivalent), Ni (divalent), Cu (monovalent or divalent), Zn (divalent). Specific examples of the transition metal compound include scandium iodide (trivalent) and the like as a scandium compound, titanium chloride (tetravalent), titanium tetraisopropoxide (tetravalent) and the like as titanium compounds, acetylacetone vanadium (trivalent), divanadium tetraoxide (tetravalent), vanadylacetyl acetonate (tetravalent), vanadium stearate oxide (tetravalent), vanadyl oxalate (tetravalent), vanazyl sulfate (tetravalent), oxobis (1-phenyl-1,3-butandionate) vanadium (tetravalent), bis (maltlate) oxovanadium (tetravalent), vanadium pentoxide (pentavalent), sodium metavanadate (pentavalent) and the like as a vanadium compound, manganese acetate (divalent), manganese naphthenate (divalent) and the like as manganese compounds, iron acetate (divalent), iron chloride (divalent), iron acetate (trivalent), iron chloride (trivalent) and the like as an iron compound, cobalt acetate (divalent), cobalt naphthenate (divalent) and the like as a cobalt compound, nickel chloride (divalent) and the like as a nickel compound, copper chloride (monovalent), copper bromide (monovalent), copper chloride (divalent), copper acetate (divalent) and the like as a copper compound, and zinc chloride (divalent), zinc acetate (divalent) and the like as a zinc compound.

Among these, a trivalent or tetravalent vanadium compound and a divalent copper compound are preferable. Among them, because of having higher polymerization accelerating ability, a trivalent or tetravalent vanadium compound is more preferable, and a tetravalent vanadium compound is most preferable. A plurality of kinds of these transition metal compounds in the period 4 in the periodic table may be used in combination, if necessary. The compounding amount of transition metal compound is preferably 0.0001 to 1 parts by mass with respect to 100 parts by mass of the total amount of the (A) polymerizable monomer. When the compounding amount is less than 0.0001 parts by mass, there is a case where the polymerization accelerating effect is insufficient, and when the compounding amount exceeds 1 part by mass, there is a case where it causes discoloration or gelation of the dental photocurable composition and the storage stability is lowered.

Any known thiourea derivatives can be used as the thiourea derivative as the chemical polymerization accelerator without any limitation. Specific examples of the thiourea derivatives include dimethylthiourea, diethylthiourea, tetramethylthiourea, (2-pyridyl) thiourea, N-methylthiourea, ethylenethiourea, N-allylthiourea, N-allyl-N'-(2-hydroxyethyl) thiourea, N-benzylthiourea, 1,3-dicyclohexyl thiourea, N,N'-diphenylthiourea, 1,3-di (p-tolyl) thiourea, 1-methyl-3-phenylthiourea, N-acetylthiourea, N-benzoylthiourea, diphenylthiourea, dicyclohexylthiourea and the like. Among these, (2-pyridyl) thiourea, N-acetylthiourea and N-benzoylthiourea are preferable. A plurality of kinds of these thiourea derivatives can be used in combination, if necessary. The compounding amount of the thiourea derivative is preferably 0.1 to 5 parts by mass with respect to 100 parts by mass of the total amount of the (A) polymerizable monomers. When the compounding amount is less than 0.1 parts by mass, there is a case where the ability as a polymerization accelerator is insufficient, and when the compounding amount exceeds 5 parts by mass, the storage stability may be lowered.

Examples of sulfinic acid and its salt include p-toluene sulfinic acid, sodium p-toluene sulfinate, potassium p-toluene sulfinate, lithium p-toluene sulfinate, calcium p-toluene sulfinate, benzenesulfinic acid, sodium benzene sulfinate, potassium benzene sulfinate, lithium benzenesulfinate, calcium benzenesulfinate, 2,4,6-trimethyl benzenesulfinic acid, sodium 2,4,6-trimethyl benzenesulfinate, potassium 2,4,6-trimethyl benzenesulfinate, lithium 2,4,6-trimethyl benzenesulfinate, calcium 2,4,6-trimethyl benzenesulfinate, 2,4,6-triethyl benzenesulfinic acid, sodium 2,4,6-triethyl benzenesulfinate, potassium 2,4,6-triethyl benzenesulfinate, lithium 2,4,6-triethyl benzenesulfinate, calcium 2,4,6-triethyl benzenesulfinate, 2,4,6-triisopropyl benzenesulfinic acid, sodium 2,4,6-triisopropyl benzenesulfinate, potassium 2,4,6-triisopropyl benzenesulfinate, lithium 2,4,6-triisopropyl benzenesulfinate, calcium 2,4,6-triisopropyl benzenesulfinate and the like. Among them, sodium benzenesulfinate, sodium p-toluenesulfinate, and sodium 2,4,6-triisopropyl benzenesulfinate are particularly preferable.

As the borate compound, specific examples of the borate compound having one aryl group in one molecule include trialkylphenylboron, trialkyl (p-chlorophenyl) boron, trialkyl (p-fluorophenyl) boron, trialkyl (3,5-bistrifluoro methyl) phenyl boron, trialkyl [3,5-bis (1,1,1,3,3,3-hexafluoro-2-methoxy-2-propyl) phenyl] boron, trialkyl (p-nitrophenyl) boron, trialkyl (m-nitrophenyl) boron, trialkyl (p-butylphenyl) boron, trialkyl (m-butylphenyl) boron, trialkyl (p-butyloxyphenyl) boron, trialkyl (m-butyloxyphenyl) boron, trialkyl (p-octyloxyphenyl) boron and trialkyl (m-octyloxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having two aryl groups in one molecule include dialkyl diphenylboron, dialkyl di (p-chlorophenyl) boron, dialkyl di (p-fluorophenyl) boron, dialkyl di (3,5-bistrifluoro methyl) phenyl boron, dialkyl di [3,5-bis (1,1,1,3,3,3-hexafluoro-2-methoxy-2-propyl) phenyl] boron, dialkyl di (p-nitrophenyl) boron, dialkyl di (m-nitrophenyl) boron, dialkyl di (p-butylphenyl) boron, dialkyl di (m-butylphenyl) boron, dialkyl di (p-butyl oxyphenyl) boron, dialkyl di (m-butyl oxyphenyl) boron, dialkyl di (p-octyl oxyphenyl) boron and dialkyl di (m-octyl oxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having three aryl groups in one molecule include monoalkyl triphenylboron, monoalkyl tri (p-chlorophenyl) boron, monoalkyl tri (p-fluorophenyl) boron, monoalkyl tri (3,5-bistrifluoro methyl) phenyl boron, monoalkyl tri [3,5-bis (1,1,1,3,3,3-hexafluoro-2-methoxy-2-propyl) phenyl] boron, monoalkyl tri (p-nitrophenyl) boron, monoalkyl tri (m-nitrophenyl) boron, monoalkyl tri (p-butylphenyl) boron, monoalkyl tri (m-butylphenyl) boron, monoalkyl tri (p-butyl oxyphenyl) boron, monoalkyl tri (m-butyl oxyphenyl) boron, monoalkyl tri (p-octyl oxyphenyl) boron and monoalkyl tri (m-octyl oxyphenyl) boron (the alkyl group is at least one selected from the group consisting of n-butyl group, n-octyl group and n-dodecyl group etc.) and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like). Specific examples of the borate compound having four aryl groups in one molecule include tetraphenylboron, tetra kis (p-chlorophenyl) boron, tetra kis (p-fluorophenyl) boron, tetra kis (3,5-bistrifluoro methyl) phenyl boron, tetra kis [3,5-bis (1,1,1,3,3,3-hexafluoro-2-methoxy-2-propyl) phenyl] boron, tetra kis (p-nitrophenyl) boron, tetra kis (m-nitrophenyl) boron, tetra kis (p-butylphenyl) boron, tetra kis (m-butylphenyl) boron, tetra kis (p-butyl oxyphenyl) boron, tetra kis (m-butyl oxyphenyl) boron, tetra kis (p-octyl oxyphenyl) boron, tetra kis (m-octyl oxyphenyl) boron, (p-fluorophenyl) triphenylboron, (3,5-bis trifluoromethyl) phenyl triphenylboron, (p-nitrophenyl) triphenylboron, (m-butyl oxyphenyl) triphenylboron, (p-butyl oxyphenyl) triphenylboron, (m-octyl oxyphenyl) triphenylboron and (p-octyl oxyphenyl) triphenylboron, and salts thereof (sodium salt, lithium salt, potassium salt, magnesium salt, tetrabutyl ammonium salt, tetramethyl ammonium salt, tetraethyl ammonium salt, methyl pyridinium salt, ethyl pyridinium salt, butyl pyridinium salt, methyl quinolinium salt, ethyl quinolinium salt, butyl quinolinium salt and the like).

Among these aryl borate compounds, it is more preferable to use a borate compound having 3 or 4 aryl groups in one molecule from the viewpoint of storage stability. Further, these aryl borate compounds can be used alone or as a mixture of two or more.

Examples of sulfur-containing reductive inorganic compound include sulfites, bisulfites, pyrosulfites, thiosulfates, thionates and dithionite. Specific examples include sodium sulfite, potassium sulfite, calcium sulfite, ammonium sulfite, sodium bisulfite, potassium bisulfite, 3-mercaptopropyl trimethoxysilane, 2-mercaptobenzoxazole, decanethiol, thiobenzoic acid and the like.

Examples of nitrogen-containing reductive inorganic compound include nitrites, and specific examples include sodium nitrite, potassium nitrite, calcium nitrite, ammonium nitrite and the like.

Specific examples of barbituric acid derivative include salts (alkali metals or alkaline earth metals are preferred) of barbituric acid, 1,3-dimethyl barbituric acid, 1,3-diphenyl barbituric acid, 1,5-dimethyl barbituric acid, 5-butyl barbituric acid, 5-ethyl barbituric acid, 5-isopropyl barbituric acid, 5-cyclohexyl barbituric acid, 1,3,5-trimethyl barbituric acid, 1,3-dimethyl-5-ethyl barbituric acid, 1,3-dimethyl-n-butyl barbituric acid, 1,3-dimethyl-5-isobutyl barbituric acid, 1,3-dimethyl barbituric acid, 1,3-dimethyl-5-cyclopentyl barbituric acid, 1,3-dimethyl-5-cyclohexyl barbituric acid 1,3-dimethyl-5-phenyl barbituric acid, 1-cyclohexyl-1-ethyl barbituric acid, 1-benzyl-5-phenyl barbituric acid, 5-methyl barbituric acid, 5-propyl barbituric acid, 1,5-diethyl barbituric acid, 1-ethyl-5-methyl barbituric acid, 1-ethyl-5-isobutyl barbituric acid, 1,3-diethyl-5-butyl barbituric acid, 1-cyclohexyl-5-methyl barbituric acid, 1-cyclohexyl-5-ethyl barbituric acid, 1-cyclohexyl-5-octyl barbituric acid, 1-cyclohexyl-5-hexyl barbituric acid, 5-butyl-1-cyclohexyl barbituric acid, 1-benzyl-5-phenyl barbituric acid and thiobarbituric acids. Specifically, the salts of these barbituric acids include sodium 5-butyl barbiturate, sodium 1,3,5-trimethyl barbiturate, sodium 1-cyclohexyl-5-ethyl barbiturate and the like.

Specific examples of the halogen compound include dilauryl dimethyl ammonium chloride, lauryl dimethyl benzyl ammonium chloride, benzyl trimethyl ammonium chloride, tetramethyl ammonium chloride, benzyl dimethyl acetyl ammonium chloride, dilauryl dimethyl ammonium bromide and the like.

The dental photocurable composition of the present disclosure may not contain a chemical polymerization initiator and a chemical polymerization accelerator. The photocurable composition of the present disclosure may not contain a polymerization initiator system other than the photopolymerization system.

<Other Component>

Further, the dental photocurable composition of the present disclosure may contain a component other than above described (A) to (D) components within a range not to impair the effect of the present disclosure. For example, an excipient typified by fumed silica, benzophenone-based and benzotriazole-based ultraviolet absorbers, polymerization inhibitors such as hydroquinone, hydroquinone monomethyl ether and 2,5-ditershally butyl-4-methylphenol, chain transfer materials such as α-alkylstyrene compound, mercaptan compound such as n-butyl mercaptan and n-octyl mercaptan, and terpenoid compound such as limonene, myrsen, α-terpinene, β-terpinene, γ-terpinene, terpinoren, β-pinene and α-pinene, metal supplementary material such as aminocarboxylic acid chelating agent and phosphonic acid chelating agent, discoloration inhibitors, antibacterial materials, coloring pigments, water and solvent that can be mixed with water in any ratio, and other additives conventionally known in the art may be added as necessary and as desired.

When the dental photocurable composition of the present disclosure contains a colorant such as a pigment, the change of color tone between before curing and after curing may be smaller than that in a case where the colorant is not contained. However, in any case, the change of color tone between before curing and after curing is is small compared with conventional photopolymerization initiator, and it can be expected that sufficient mechanical properties will be exhibited for dental applications.

A preparing method of the dental photocurable composition of the present disclosure is not particularly limited. Examples of a general preparing method of a dental photocurable composition include a method which comprises preparing a matrix by mixing (A) polymerizable monomer, (B) photosensitizer, (C) photoacid generator and (D) photopolymerization accelerator in advance, kneading the matrix and (E) filler, and removing air bubbles under vacuum to prepare a uniform paste. In the present disclosure, it can be prepare by the above-described method without any problem.

The dental photocurable composition of the present disclosure is applied to a dental adhesive material, a dental composite resin, a dental core build-up material, a dental resin cement, a dental coating material, a dental sealant material, a dental manicure material, a dental splinting material, a dental hard resin, a dental CAD-CAM restoration material, a dental 3D printer material and the like.

In the present disclosure, it is preferable that a difference between b* value before curing which may be obtained by color measuring a color tone in the L*a*b* color space for a 1-mm-thick dental photocurable composition (or a dental photocurable composition in which a pigment is excluded when the dental photocurable composition contains the pigment) on a white background and b* value after curing which may be obtained by color measuring a color tone in the L*a*b* color space for a 1-mm-thick cured body of the dental photocurable composition on a white background is less than 4. In the present disclosure, the color tone before curing is measured after filling the dental photocurable composition into a stainless mold (15φ×1 mm: disk shape), placing a cover glass that is colorless and transparent, and has a thickness of 170 μm or less from the top, and confirming that the dental photocurable composition is in a uniform state without containing air bubbles. Subsequently, light irradiation is performed on the cover glass for 1 minutes using a photopolymerization irradiator (Grip Light II, manufactured by SHOFU Inc.) to prepare a cured material and the cured material was taken out of the mold as a test specimen and was measured for color tone as the color tone after curing. Color measurement was performed by placing the test specimen on the background of a standard white plate (D65/10°, X=81.07, Y=86.15, Z=93.38) and using a spectrocolorimeter (manufactured by BYK-Chemie GmbH) under predetermined condition (light source: C, viewing angle: 2°, measurement area: 11 mm).

<One Pack Type Dental Photocurable Composition>

When the dental photocurable composition of the present disclosure is used for one pack type dental photocurable composition, particularly as dental materials, it is preferable to use for a dental adhesive material, a dental composite resin, a dental core build-up material, a dental resin cement, a dental coating material, a dental sealant material, a dental manicure material, a dental splinting material, a dental hard resin, a dental CAD-CAM restoration material and a dental 3D printer material, it is particularly preferable to use for a dental adhesive material, a dental composite resin, a dental core build-up material, a dental resin cement, a dental coating material, a dental sealant material, a dental manicure material, a dental splinting material and a dental hard resin. In the case of a one pack type dental photocurable composition, it can be expected that there are few technical errors and the risk of contamination with air bubbles is reduced.

<Two Packs Type Dental Photocurable Composition>

When the dental photocurable composition of the present disclosure is used for two packs type dental photocurable composition, particularly as dental materials, it is preferable to use for a dental adhesive material, a dental composite resin, a dental core build-up material, a dental resin cement, a dental coating material, a dental sealant material, a dental manicure material, a dental splinting material, a dental hard resin, a dental CAD-CAM restoration material and a dental 3D printer material, it is particularly preferable to use for a dental adhesive material, a dental composite resin, a dental core build-up material and a dental resin cement. The two packs type dental material is used by kneading the two packs including a first paste and a second paste immediately before use. The kneading is performed by mixing the first paste and the second paste in a volume ratio of 0.9 to 1.1:1.0 or a mass ratio of 0.8 to 1.2:1.0, preferably an equal volume ratio. The kneading method may be a known method such as manual kneading using a dedicated shaking device or a spatula, or automatic kneading via a static mixer. Since the components can be separated into two packs, compounds that cannot be compounded in the same paste can be compounded separately, therefore the storage stability is excellent.

The dental photocurable composition of the present disclosure may comprise only (A) polymerizable monomer, (B) photosensitizer, (C) photoacid generator, (D) photopolymerization accelerator and (E) filler. Further, as the components other than (A) to (E), only one or more of the above-mentioned components may be contained.

EXAMPLES

Hereinafter, example of the present disclosure are specifically described. However, the present disclosure is not intended to be limited to these Examples.

The materials used in Examples and Comparative examples and their abbreviations are listed below.

[(A) Polymerizable Monomer]
Bis-GMA: 2,2-bis [4-(3-methacryloyloxy-2-hydroxypropoxy) phenyl] propane
D2.6E: 2,2-bis (4-(meth) acryloyloxy polyethoxyphenyl) propane in which the average addition mole number of ethoxy groups is 2.6
UDMA: N,N-(2,2,4-trimethyl hexamethylene) bis [2-(aminocarboxy) ethanol]methacrylate
TEGDMA: triethyleneglycol dimethacrylate
NPG: neopentyl glycol dimethacrylate
MDP: 10-methacryloyloxydecyl dihydrogen phosphate
MHPA: 6-methacryloyloxyhexyl phosphonoacetate
[(B) Photosensitizer Other than (b-1) α-Diketones]
BAPO: phenyl bis (2,4,6-trimethylbenzoyl) phosphine oxide
[(B-1) α-diketones]
CQ: camphorquinone
CQ-COOH: camphorquinone carboxylic acid
[(C) Photoacid Generator]
<Salt of an Anion Having an Organic Group and One or More Atoms of P, B, Al, S, and Ga, and an Aryl Iodonium Cation>

C1: bis (4-tert-butylphenyl) iodonium-p-toluenesulfonate

[Chemical formula 1]

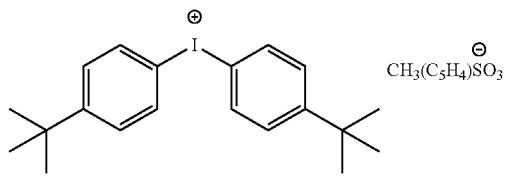

C2: bis (4-tert-butylphenyl) iodium camphor sulfonate

[Chemical formula 2]

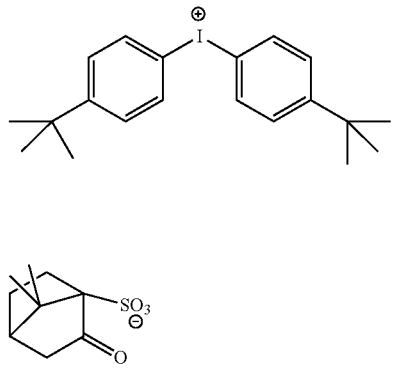

<Salt of an Anion Having an Organic Group in which at Least One H is Substituted with F and One or More Atoms of P, B, Al, S, and Ga, and an Aryl Iodonium Cation>

C3: bis (4-tert-butylphenyl) iodonium nonafluorobutane sulfonate

[Chemical formula 3]

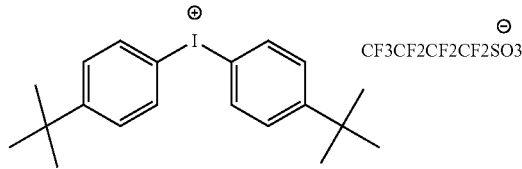

C4: bis (4-tert-butylphenyl) iodonium tris (pentafluoropropyl) trifluorophosphate

[Chemical formula 4]

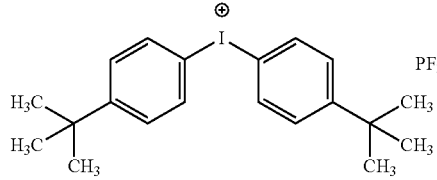

C8: bis (4-tert-butylphenyl) iodonium tris (trifluoromethane sulfonyl) methide

[Chemical formula 8]

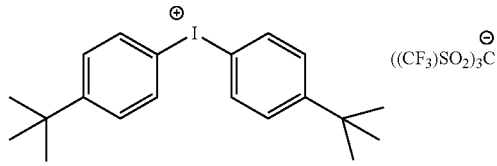

C5: p-cumenyl (p-tolyl) iodonium tris (pentafluoroethyl) trifluorophosphate

[Chemical formula 5]

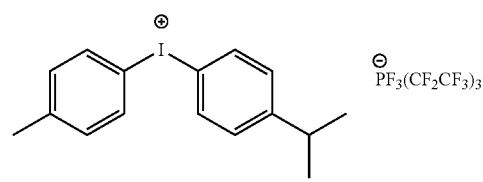

C9: bis (4-tert-butylphenyl) iodonium-o-trifluoromethyl benzenesulfonate

[Chemical formula 9]

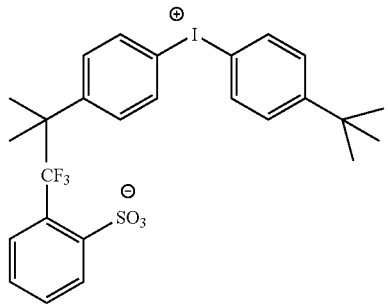

C6: bis (4-tert-butylphenyl) iodonium tetra (nonafluoro-tert-butoxy) aluminate

[Chemical formula 6]

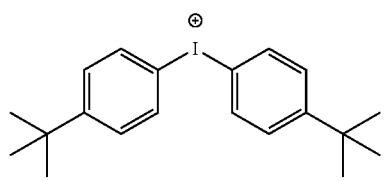

C10: di (bis (4-tert-butylphenyl) iodonium) octafluorobutane disulfonate

[Chemical formula 10]

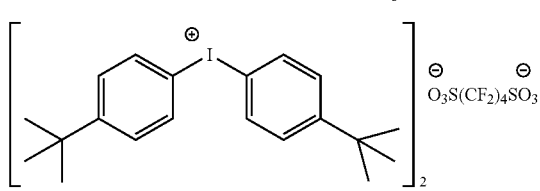

C7: di-p-tolyleiodonium phenyl tris (pentafluorophenyl) borate

[Chemical formula 7]

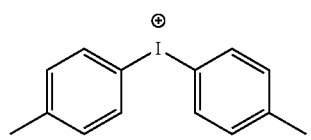

C11: bis [4-(tert-butyl) phenyl] iodonium tetra (pentafluorophenyl) gallate

[Chemical formula 11]

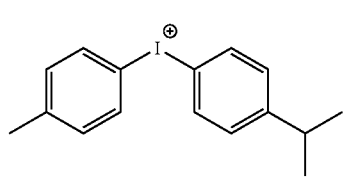

C12: bis (4-n-dodecylphenyl) iodonium tetrakis (pentafluorophenyl) borate

[Chemical formula 12]

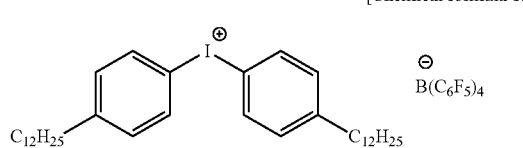

<Photoacid Generator that is not a Salt of an Anion Having an Organic Group and an Aryliodonium Cation>

C13: bis (4-tert-butylphenyl) iodonium hexafluorophosphate

[Chemical formula 13]

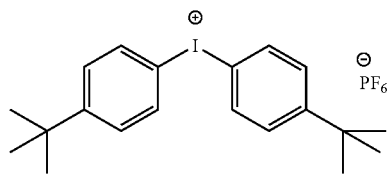

C14: 2,4,6-tris (trichloromethyl)-1,3,5-triazine

[Chemical formula 14]

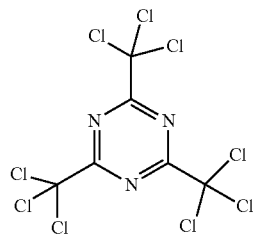

C15: diphenyliodonium-2-carboxylate monohydrate

[Chemical formula 15]

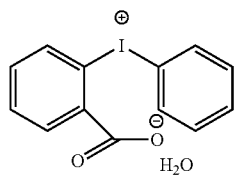

[(D) Photopolymerization Accelerator]
<Alphatic Tertiary Amine>
<<Aliphatic Tertiary Amine Compound Having No Primary Hydroxyl Group>>
TBA: tribenzylamine
DBGE: N,N-dibenzyl glycine ethyl
DEAEMA: N,N-diethylamino ethylmethacrylate
DMAEMA: N,N-dimethylamino ethylmethacrylate
<<Aliphatic Tertiary Amine Compound Having One Primary Hydroxyl Group>>
DBAE: N,N-dibenzylamino ethanol
<<Aliphatic Tertiary Amine Compound Having Two Primary Hydroxyl Groups>>
MDEOA: methyl diethanolamine
<<Aliphatic Tertiary Amine Compound Having Three Primary Hydroxyl Groups>>
TEA: triethanolamine
<Aromatic Tertiary Amine Compound>
DMBE: N,N-dimethylaminobenzoate ethyl
DEPT: N,N-dihydroxyethyl-p-toluidine
DMPT: N,N-dimethyl-p-toluidine
<Organic Metal Compound>
DBTL: dibutyl-tin-dilaurate
[(E) Filler]
The preparing method of each filler used for preparing the dental photocurable composition is shown below.
(Filler 1)
A silane coupling treatment solution prepared by stirring 50.0 g of water, 35.0 g of ethanol, and 3.0 g of 3-methacryloyloxypropyl trimethoxysilane as a silane coupling agent at room temperature for 2 hours was added to 100.0 g of the fluoroaluminosilicate glass (average particle diameter: 0.9 μm) and stirred for 30 minutes. Thereafter, a heat treatment was performed at 100° C. for 15 hours to obtain a filler 1.
(Filler 2)
A silane coupling treatment solution prepared by stirring 50.0 g of water, 35.0 g of ethanol, and 5.0 g of 3-methacryloyloxypropyl trimethoxysilane as a silane coupling agent at room temperature for 2 hours was added to 100.0 g of the zirconium silicate glass (average particle diameter: 0.8 μm, zirconia: 85 wt. %, silica: 15 wt. %) and stirred for 30 minutes. Thereafter, a heat treatment was performed at 100° C. for 15 hours to obtain a filler 2.
[Chemical Polymerization Initiator]
CHP: cumene hydroperoxide
BPO: benzoyl peroxide
[Chemical Polymerization Accelerator]
PTU: (2-pyridyl) thiourea
DEPT: N,N-dihydroxyethyl-p-toluidine
DMPT: N,N-dimethyl-p-toluidine
COA: acetylacetone copper
VOA: vanadyl acetylacetonate
[Uv Absorber]
BT: 2-(2-hydroxy-5-methylphenyl) benzotriazole
[Polymerization Inhibitor]
BHT: 2,6-di-t-butyl-4-methylphenol
MeHQ: p-methoxyphenol
[Fluorescent Agent]
FA: 2,5-dihydroxyterephthalate diethyl
<Preparing Method of One Pack Type Dental Photocurable Composition>
All component shown in Table 1 other than the filler (E) were put into a wide mouthed plastic container and mixed by using a mix rotor VMRC-5 under the condition of 100 rpm for 48 hours to prepare a matrix. Then, the matrix and the filler (E) were put into a kneader, stirred uniformly, and then defoamed under vacuum to prepare a dental photocurable composition. In the table, the content (parts by mass) of each component is indicated by the numerical value in parentheses after the abbreviation of each component.

TABLE 1

|  | (A) Polymerizable monomer | (B) Photosensitizer | | (C) Photoacid generator |
|---|---|---|---|---|
|  |  | (B-1) | Other than (B-1) |  |
| Example A1 | Bis-GMA(60), TEGDMA(40) | CQ(0.005) | — | C3(0.5) |
| Example A2 | Bis-GMA(60), TEGDMA(40) | CQ(0.04) | — | C4(1) |
| Example A3 | Bis-GMA(60), TEGDMA(40) | CQ(0.05) | — | C5(1) |
| Example A4 | Bis-GMA(60), TEGDMA(40) | CQ(0.075) | — | C6(1) |
| Example A5 | Bis-GMA(60), TEGDMA(40) | CQ(0.10) | — | C7(1) |
| Example A6 | Bis-GMA(60), TEGDMA(40) | CQ(0.11) | — | C7(2.0) |
| Example A7 | Bis-GMA(60), TEGDMA(40) | CQ(0.12) | — | C2(2.0) |
| Example A8 | D2.6E(80), TEGDMA(20) | CQ(0.15) | — | C3(2.0) |
| Example A9 | Bis-GMA(60), TEGDMA(40) | CQ(0.10) | — | C6(0.5) |
| Example A10 | Bis-GMA(60), TEGDMA(40) | CQ(0.10) | — | C6(0.8) |
| Example A11 | Bis-GMA(40), UDMA(30), TEGDMA(30) | CQ(0.10) | — | C6(5.5) |
| Example A12 | Bis-GMA(40), UDMA(30), TEGDMA(30) | CQ(0.10) | — | C6(8) |
| Example A13 | Bis-GMA(40), UDMA(30), TEGDMA(30) | CQ(0.10) | — | C6(10.0) |
| Example A14 | Bis-GMA(40), UDMA(30), TEGDMA(30) | CQ(0.10) | — | C7(2.0) |
| Example A15 | Bis-GMA(60), TEGDMA(40) | CQ(0.10) | — | C7(2.0) |
| Example A16 | Bis-GMA(40), UDMA(20), NPG(40) | CQ(0.10) | — | C7(2.0) |
| Example A17 | Bis-GMA(40), UDMA(20), NPG(40) | CQ(0.10) | — | C7(2.0) |
| Example A18 | Bis-GMA(60), TEGDMA(40) | CQ(0.10) | — | C7(2.0) |
| Example A19 | Bis-GMA(60), TEGDMA(40) | CQ(0.15 | — | C7(10.0) |
| Example A20 | Bis-GMA(60), TEGDMA(40) | CQ(0.10) | — | C9(1.5) |
| Example A21 | Bis-GMA(60), TEGDMA(40) | CQ(0.10) | — | C10(1.5) |
| Example A22 | Bis-GMA(40), UDMA(20), NPG(40) | CQ(0.10) | — | C9(1.5) |
| Example A23 | Bis-GMA(60), TEGDMA(40) | CQ(0.10) | — | C10(1.5) |
| Example A24 | Bis-GMA(40), UDMA(20), NPG(40) | CQ(0.10) | — | C8(2.0) |
| Example A25 | Bis-GMA(60), TEGDMA(40) | CQ(0.10) | — | C2(2.0) |
| Example A26 | Bis-GMA(60), TEGDMA(40) | CQ(0.10) | — | C2(2.0) |
| Example A27 | Bis-GMA(60), TEGDMA(20), MDP(20) | CQ(0.11) | — | C1(2.0) |
| Example A28 | Bis-GMA(60), TEGDMA(20), MHPA(20) | CQ(0.10) | — | C1(1.0) |
| Example A29 | Bis-GMA(60), TEGDMA(40) | CQ(0.10) | — | C13(1) |
| Example A30 | Bis-GMA(60), TEGDMA(40) | CQ(0.10) | — | C14(1) |
| Example A31 | Bis-GMA(60), TEGDMA(40) | CQ(0.10) | — | C15(1) |
| Example A32 | Bis-GMA(60), TEGDMA(40) | CQ(0.10) | — | C13(5) |
| Example A33 | Bis-GMA(40), UDMA(20), NPG(40) | CQ(0.10) | — | C14(5) |
| Example A34 | Bis-GMA(60), TEGDMA(40) | CQ(0.10) | — | C15(5) |
| Example A35 | Bis-GMA(40), UDMA(20), NPG(40) | CQ(0.10) | — | C1(1) |
| Example A36 | Bis-GMA(60), TEGDMA(40) | CQ(0.10) | — | C2(1) |
| Example A37 | Bis-GMA(40), UDMA(20), NPG(40) | CQ(0.10) | — | C1(7) |
| Example A38 | Bis-GMA(60), TEGDMA(40) | CQ(0.10) | — | C2(8) |
| Example A39 | Bis-GMA(60), TEGDMA(40) | CQ(0.10) | — | C8(1) |
| Example A40 | Bis-GMA(40), UDMA(20), NPG(40) | CQ(0.10) | — | C9(1) |
| Example A41 | Bis-GMA(60), TEGDMA(40) | CQ(0.10) | — | C8(1) |
| Example A42 | Bis-GMA(40), UDMA(20), NPG(40) | CQ(0.10) | — | C9(1) |
| Example A43 | Bis-GMA(60), TEGDMA(40) | CQ(0.10) | — | C10(2.0) |
| Example A44 | Bis-GMA(60), TEGDMA(40) | CQ(0.10) | — | C10(2.0) |
| Example A45 | Bis-GMA(60), TEGDMA(40) | CQ(0.10) | — | C10(2.0) |
| Example A46 | Bis-GMA(60), TEGDMA(40) | CQ(0.10) | — | C10(2.0) |
| Example A47 | Bis-GMA(40), UDMA(20), NPG(40) | CQ(0.08) | — | C11(2.0) |
| Example A48 | Bis-GMA(60), TEGDMA(40) | CQ(0.005) | — | C6(0.5) |
| Example A49 | Bis-GMA(60), TEGDMA(40) | CQ(0.01) | — | C7(0.5) |
| Example A50 | Bis-GMA(40), UDMA(20), NPG(40) | CQ(0.15) | — | C3(2.0) |
| Example A51 | Bis-GMA(40), UDMA(20), NPG(40) | CQ(0.15) | — | C5(10.0) |
| Example A52 | Bis-GMA(60), TEGDMA(40) | CQ(0.04) | — | C5(1) |
| Example A53 | Bis-GMA(60), TEGDMA(40) | CQ(0.075) | — | C5(1) |
| Example A54 | Bis-GMA(60), TEGDMA(40) | CQ(0.10) | — | C5(2) |
| Example A55 | Bis-GMA(60), TEGDMA(40) | CQ(0.11) | — | C4(2.5) |
| Example A56 | Bis-GMA(60), TEGDMA(40) | CQ(0.10) | — | C5(1.5) |
| Example A57 | Bis-GMA(60), TEGDMA(40) | CQ(0.10) | — | C6(1.5) |
| Example A58 | Bis-GMA(60), TEGDMA(40) | CQ(0.10) | — | C6(1.5) |
| Example A59 | Bis-GMA(60), TEGDMA(40) | CQ(0.10) | — | C10(1.5) |
| Example A60 | Bis-GMA(60), TEGDMA(40) | CQ(0.003) | — | C3(0.5) |
| Example A61 | Bis-GMA(40), UDMA(30), TEGDMA(30) | CQ(0.10) | — | C6(12.0) |
| Example A62 | Bis-GMA(40), UDMA(20), NPG(40) | CQ(0.08) | — | C11(3.0) |
| Example A63 | Bis-GMA(40), UDMA(30), TEGDMA(30) | CQ(0.08) | — | C11(2.0) |
| Example A64 | Bis-GMA(60), TEGDMA(40) | CQ(0.10) | — | C14(1) |
| Example A65 | Bis-GMA(60), TEGDMA(40) | CQ(0.075) | — | C5(1) |
| Example A66 | Bis-GMA(60), TEGDMA(40) | CQ(0.005) | — | C3(0.5) |
| Example A67 | Bis-GMA(60), TEGDMA(40) | CQ(0.10) | — | C7(2.0) |
| Example A68 | Bis-GMA(60), TEGDMA(40) | CQCOOH(0.10) | — | C5(1) |
| Example A69 | Bis-GMA(60), TEGDMA(40) | CQ(0.10) | — | C4(1) |
| Example A70 | Bis-GMA(60), TEGDMA(40) | CQ(0.10) | — | C4(5) |
| Comparative Example CA1 | Bis-GMA(60), TEGDMA(40) | — | — | C7(2.0) |
| Comparative Example CA2 | Bis-GMA(60), TEGDMA(40) | CQ(0.18) | — | C7(2.0) |

TABLE 1-continued

| | | | | |
|---|---|---|---|---|
| Comparative Example CA3 | Bis-GMA(60), TEGDMA(40) | CQ(0.30) | — | C7(2.0) |
| Comparative Example CA4 | Bis-GMA(60), TEGDMA(40) | CQ(0.30) | — | C7(2.0) |
| Comparative Example CA5 | Bis-GMA(60), TEGDMA(40) | CQ(0.10) | — | C7(0.4) |
| Comparative Example CA6 | Bis-GMA(60), TEGDMA(40) | CQ(0.10) | — | C7(2.0) |
| Comparative Example CA7 | Bis-GMA(60), TEGDMA(40) | CQ(0.15) | — | C10(3) |
| Comparative Example CA8 | Bis-GMA(60), TEGDMA(40) | CQ(0.10) | — | C10(3) |
| Comparative Example CA9 | Bis-GMA(60), TEGDMA(40) | CQ(0.15) | — | C10(3) |
| Comparative Example CA10 | Bis-GMA(60), TEGDMA(40) | CQ(0.10) | — | C10(3) |
| Comparative Example CA11 | Bis-GMA(60), TEGDMA(40) | — | BAPO(0.1) | C1(1.0) |
| Comparative Example CA12 | Bis-GMA(60), TEGDMA(40) | CQ(0.30) | — | C7(2.0) |

| | (D) Photopolymerization accelerator | | | | |
|---|---|---|---|---|---|
| | (D-1) | Other than (D-1) | (E) Filler | Polymerization inhibitor | Others |
| Example A1 | TBA(0.1) | — | Filler 1(100) | MeHQ(0.005) | FA(0.05) |
| Example A2 | DBGE(0.5) | — | Filler 2(100) | MeHQ(0.01) | FA(0.05) |
| Example A3 | DMAEMA(0.75) | — | Filler 1(100) | MeHQ(0.005) | — |
| Example A4 | DBGE(2) | — | Filler 1(100) | MeHQ(0.01) | — |
| Example A5 | TBA(0.75) | — | Filler 1(100) | MeHQ(0.01) | FA(0.05) |
| Example A6 | DEAEMA(2) | — | Filler 1(100) | MeHQ(0.005) | — |
| Example A7 | TBA(0.75) | — | Filler 2(100) | MeHQ(0.01) | — |
| Example A8 | DBGE(2) | — | Filler 1(100) | BHT(0.005) | FA(0.05) |
| Example A9 | DEAEMA(2) | — | Filler 1(100) | MeHQ(0.01) | — |
| Example A10 | TBA(0.75) | — | Filler 2(100) | MeHQ(0.005) | — |
| Example A11 | TBA(0.75) | — | Filler 1(100) | MeHQ(0.01) | — |
| Example A12 | TBA(0.75) | — | Filler 1(100) | BHT(0.005) | FA(0.05) |
| Example A13 | DBGE(2) | — | Filler 1(100) | MeHQ(0.005) | — |
| Example A14 | TBA(0.1) | — | Filler 1(100) | MeHQ(0.005) | — |
| Example A15 | TBA(0.4) | — | Filler 2(100) | BHT(0.08) | — |
| Example A16 | DBGE(5) | — | Filler 1(100) | MeHQ(0.005) | FA(0.05) |
| Example A17 | DBGE(15) | — | Filler 1(100) | MeHQ(0.005) | — |
| Example A18 | DBGE(20) | — | Filler 1(100) | MeHQ(0.005) | — |
| Example A19 | TBA(20) | — | Filler 2(100) | MeHQ(0.005) | FA(0.05) |
| Example A20 | — | DMBE(0.5) | Filler 1(100) | BHT(0.08) | — |
| Example A21 | — | DMPT(0.5) | Filler 2(100) | MeHQ(0.005) | — |
| Example A22 | — | DMBE(0.5) | Filler 1(100) | MeHQ(0.005) | BT(0.5) |
| Example A23 | — | DMPT(0.5) | Filler 1(100) | BHT(0.08) | BT(0.5) |
| Example A24 | DBAE(1) | — | Filler 1(100) | MeHQ(0.005) | — |
| Example A25 | — | MDEOA(0.5) | Filler 2(100) | MeHQ(0.005) | — |
| Example A26 | — | TEA(0.5) | Filler 1(100) | BHT(0.08) | — |
| Example A27 | DEAEMA(0.8) | — | Filler 2(100) | MeHQ(0.005) | — |
| Example A28 | DEAEMA(0.8) | — | Filler 1(250) | BHT(0.08) | — |
| Example A29 | TBA(1) | — | Filler 2(250) | MeHQ(0.005) | FA(0.05) |
| Example A30 | TBA(1) | — | Filler 1(250) | BHT(0.08) | — |
| Example A31 | TBA(1) | — | Filler 1(250) | MeHQ(0.005) | — |
| Example A32 | TBA(1) | — | Filler 2(250) | BHT(0.08) | — |
| Example A33 | TBA(1) | — | Filler 1(250) | MeHQ(0.005) | FA(0.05) |
| Example A34 | TBA(1) | — | Filler 1(250) | MeHQ(0.005) | — |
| Example A35 | DEAEMA(0.8) | — | Filler 1(250) | MeHQ(0.01) | FA(0.05) |
| Example A36 | DEAEMA(0.8) | — | Filler 2(250) | MeHQ(0.01) | — |
| Example A37 | DEAEMA(0.8) | — | Filler 1(250) | BHT(0.08) | — |
| Example A38 | DEAEMA(0.8) | — | Filler 1(250) | MeHQ(0.01) | FA(0.05) |
| Example A39 | — | TEA(0.6) | Filler 1(250) | MeHQ(0.01) | — |
| Example A40 | — | MDEOA(0.8) | Filler 2(250) | MeHQ(0.005) | — |
| Example A41 | — | TEA(0.6) | Filler 1(250) | BHT(0.08) | — |
| Example A42 | — | MDEOA(0.7) | Filler 1(250) | MeHQ(0.005) | — |
| Example A43 | TBA(0.75) | DMBE(0.5) | Filler 2(250) | MeHQ(0.005) | FA(0.05) |
| Example A44 | TBA(2.0) | DMPT(0.5) | Filler 1(250) | MeHQ(0.005) | — |
| Example A45 | TBA(2.0) | DEPT(0.5) | Filler 2(250) | BHT(0.08) | — |
| Example A46 | — | DEPT(0.5) | Filler 1(250) | MeHQ(0.005) | — |
| Example A47 | TBA(3) | — | Filler 1(800) | MeHQ(0.005) | FA(0.05) |
| Example A48 | TBA(0.1) | — | Filler 1(800) | MeHQ(0.005) | — |
| Example A49 | TBA(0.5) | — | Filler 1(800) | BHT(0.08) | FA(0.05) |
| Example A50 | TBA(3) | — | Filler 1(800) | MeHQ(0.005) | — |
| Example A51 | TBA(20) | — | Filler 1(800) | MeHQ(0.005) | — |
| Example A52 | DEAEMA(0.75) | DMBE(0.3) | Filler 1(800) | BHT(0.08) | FA(0.05) |

TABLE 1-continued

| | | | | | |
|---|---|---|---|---|---|
| Example A53 | DBGE(2) | DMBE(0.5) | Filler 1(800) | MeHQ(0.005) | — |
| Example A54 | TBA(0.75) | DBTL(0.5) | Filler 1(800) | BHT(0.08) | — |
| Example A55 | DEAEMA(2) | — | Filler 1(800) | MeHQ(0.005) | FA(0.05) |
| Example A56 | DEAEMA(2) | — | Filler 1(800) | MeHQ(0.005) | — |
| Example A57 | — | TEA(0.7) | Filler 1(800) | BHT(0.08) | FA(0.05) |
| Example A58 | — | MDEOA(0.6) | Filler 1(800) | MeHQ(0.005) | — |
| Example A59 | TBA(1.5) | DMBE(0.5) | Filler 1(800) | MeHQ(0.005) | — |
| Example A60 | TBA(0.5) | — | Filler 1(100) | MeHQ(0.005) | FA(0.05) |
| Example A61 | DBGE(2) | — | Filler 1(100) | MeHQ(0.005) | — |
| Example A62 | TBA(3) | — | Filler 1(1000) | MeHQ(0.005) | FA(0.05) |
| Example A63 | DBGE(3) | — | Filler 1(1200) | MeHQ(0.005) | FA(0.05) |
| Example A64 | TBA(1.5) | — | Filler 1(150) | BHT(0.08) | — |
| Example A65 | DBGE(2) | DMBE(0.01) | Filler 1(800) | MeHQ(0.005) | — |
| Example A66 | TBA(0.05) | — | Filler 1(100) | MeHQ(0.005) | FA(0.05) |
| Example A67 | DBGE(25) | — | Filler 1(100) | MeHQ(0.005) | — |
| Example A68 | DMAEMA(0.75) | — | Filler 1(100) | MeHQ(0.005) | — |
| Example A69 | TBA(1) | — | Filler 1(250) | MeHQ(0.005) | — |
| Example A70 | TBA(1) | — | Filler 2(250) | BHT(0.08) | — |
| Comparative Example CA1 | DMAEMA(2) | — | Filler 1(250) | MeHQ(0.005) | FA(0.05) |
| Comparative Example CA2 | DMAEMA(2) | — | Filler 1(100) | MeHQ(0.005) | — |
| Comparative Example CA3 | DMAEMA(2) | — | Filler 1(800) | BHT(0.08) | — |
| Comparative Example CA4 | DMAEMA(2) | — | Filler 1(250) | MeHQ(0.005) | — |
| Comparative Example CA5 | DEAEMA(2) | — | Filler 1(250) | MeHQ(0.005) | FA(0.05) |
| Comparative Example CA6 | — | — | Filler 1(250) | BHT(0.08) | — |
| Comparative Example CA7 | TBA(3) | — | Filler 1(80) | MeHQ(0.005) | FA(0.05) |
| Comparative Example CA8 | TBA(3) | — | Filler 1(80) | BHT(0.08) | FA(0.05) |
| Comparative Example CA9 | TBA(3) | — | — | MeHQ(0.005) | FA(0.05) |
| Comparative Example CA10 | TBA(3) | — | — | MeHQ(0.005) | — |
| Comparative Example CA11 | DEAEMA(0.8) | — | Filler 1(250) | MeHQ(0.01) | — |
| Comparative Example CA12 | — | MDEOA(2) | Filler 1(250) | MeHQ(0.005) | — |

<Preparing Method of Two Packs Type Dental Photocurable Composition>

All component shown in Table 2 other than the filler (E) were put into a wide mouthed plastic container and mixed by using a mix rotor VMRC-5 under the condition of 100 rpm for 48 hours to prepare a matrix. Then, the matrix and the filler (E) were put into a kneader, stirred uniformly and then defoamed under vacuum to prepare a first paste and a second paste, and then the first paste and the second paste were filled into a double syringe (5 mL) manufactured by Mixpack Co., Ltd. to prepare a dental photocurable composition. When using, a paste prepared by mixing the first paste and the second paste with a mixing chip manufactured by Mixpack Co., Ltd. was used. The mixing chip manufactured by Mixpack Co., Ltd. can be mixed by a static mixer, and when using it, the first paste and the second paste can be kneaded at a volume ratio of 0.9 to 1.1:1.00, ideally at equal volumes. The first paste and the second paste were kneaded so as to have a mass ratio of 0.8 to 1.2:1.0 and used. In the table, the content (parts by mass) of each component is indicated by the numerical value in parentheses after the abbreviation of each component.

TABLE 2

| | | (A) Polymerizable monomer | (B) Photosensitizer | | (C) Photoacid generator | (D) Photopolymerization accelerator (D-1) |
|---|---|---|---|---|---|---|
| | | | (B-1) | Other than (B-1) | | |
| Example B1 | First paste | Bis-GMA(60), TEGDMA(40) | CQ(0.01) | — | — | TBA(0.2) |
| | Second paste | Bis-GMA(60), TEGDMA(40) | — | — | C3(1) | — |
| Example B2 | First paste | Bis-GMA(60), TEGDMA(40) | CQ(0.08) | — | — | DBGE(1) |
| | Second paste | Bis-GMA(60), TEGDMA(40) | — | — | C4(2) | — |
| Example B3 | First paste | Bis-GMA(60), TEGDMA(40) | CQ(0.10) | — | C5(3) | — |
| | Second paste | Bis-GMA(60), TEGDMA(40) | — | — | — | DMAEMA(1.5) |
| Example B4 | First paste | Bis-GMA(60), TEGDMA(40) | CQ(0.15) | — | C6(2) | DBGE(2) |
| | Second paste | Bis-GMA(60), TEGDMA(40) | — | — | — | — |
| Example B5 | First paste | Bis-GMA(60), TEGDMA(40) | CQ(0.30) | — | C3(4) | — |
| | Second paste | Bis-GMA(60), TEGDMA(40) | — | — | — | DBGE(4) |

TABLE 2-continued

| | | | | | | |
|---|---|---|---|---|---|---|
| Example B6 | First paste | Bis-GMA(60), TEGDMA(40) | CQ(0.20) | — | C6(1) | — |
| | Second paste | Bis-GMA(60), TEGDMA(40) | — | — | — | DEAEMA(2) |
| Example B7 | First paste | Bis-GMA(60), TEGDMA(40) | CQ(0.20) | — | C6(1.6) | — |
| | Second paste | Bis-GMA(60), TEGDMA(40) | — | — | — | TBA(1.5) |
| Example B8 | First paste | Bis-GMA(60), TEGDMA(40) | CQ(0.20) | — | C6(10) | — |
| | Second paste | Bis-GMA(60), TEGDMA(40) | — | — | — | DBGE(2) |
| Example B9 | First paste | Bis-GMA(60), TEGDMA(40) | CQ(0.20) | — | C6(15) | — |
| | Second paste | Bis-GMA(60), TEGDMA(40) | — | — | — | DBGE(2) |
| Example B10 | First paste | Bis-GMA(60), TEGDMA(40) | CQ(0.20) | — | C6(20) | — |
| | Second paste | Bis-GMA(60), TEGDMA(40) | — | — | — | DBGE(2) |
| Example B11 | First paste | Bis-GMA(60), TEGDMA(40) | CQ(0.20) | — | C7(2) | — |
| | Second paste | Bis-GMA(60), TEGDMA(40) | — | — | — | TBA(0.2) |
| Example B12 | First paste | Bis-GMA(60), TEGDMA(40) | CQ(0.20) | — | — | TBA(0.8) |
| | Second paste | Bis-GMA(60), TEGDMA(30), MDP(10) | — | — | C7(2) | — |
| Example B13 | First paste | Bis-GMA(60), TEGDMA(40) | CQ(0.20) | — | — | DBGE(30) |
| | Second paste | Bis-GMA(60), TEGDMA(40) | — | — | C7(4) | — |
| Example B14 | First paste | Bis-GMA(60), TEGDMA(40) | CQ(0.20) | — | — | DBGE(40) |
| | Second paste | Bis-GMA(60), TEGDMA(40) | — | — | C7(4) | — |
| Example B15 | First paste | D2.6E(80), TEGDMA(20) | CQ(0.30) | — | — | TBA(20) |
| | Second paste | Bis-GMA(60), TEGDMA(40) | — | — | C7(20) | TBA(20) |
| Example B16 | First paste | D2.6E(80), TEGDMA(20) | — | — | C7(2) | — |
| | Second paste | Bis-GMA(60), TEGDMA(40) | CQ(0.20) | — | — | DBAE(2.0) |
| Example B17 | First paste | D2.6E(80), TEGDMA(20) | CQ(0.20) | — | C8(4) | — |
| | Second paste | Bis-GMA(60), TEGDMA(40) | — | — | — | — |
| Example B18 | First paste | Bis-GMA(60), TEGDMA(40) | CQ(0.20) | — | — | — |
| | Second paste | Bis-GMA(60), TEGDMA(30), MHPA(10) | — | — | C6(4) | — |
| Example B19 | First paste | Bis-GMA(60), TEGDMA(40) | CQ(0.22) | — | — | DEAEMA(1.6) |
| | Second paste | Bis-GMA(60), TEGDMA(40) | — | — | C7(2) | — |
| Example B20 | First paste | Bis-GMA(60), TEGDMA(30), MHPA(10) | CQ(0.10) | — | C12(3) | — |
| | Second paste | Bis-GMA(60), TEGDMA(40) | — | — | — | DMAEMA(1.5) |
| Example B21 | First paste | Bis-GMA(60), TEGDMA(40) | CQ(0.10) | — | C11(2) | DBGE(2) |
| | Second paste | Bis-GMA(60), TEGDMA(30), MHPA(10) | — | — | — | — |
| Example B22 | First paste | Bis-GMA(60), TEGDMA(40) | CQ(0.21) | — | — | TBA(4) |
| | Second paste | Bis-GMA(60), TEGDMA(40) | — | — | C8(2) | — |
| Example B23 | First paste | Bis-GMA(60), TEGDMA(40) | CQ(0.10) | — | C5(1) | DEAEMA(0.8) |
| | Second paste | Bis-GMA(60), TEGDMA(30), MHPA(10) | CQ(0.10) | — | C7(1) | DEAEMA(0.8) |
| Example B24 | First paste | Bis-GMA(60), TEGDMA(40) | CQ(0.20) | — | C13(1) | — |
| | Second paste | Bis-GMA(60), TEGDMA(40) | — | — | — | DMAEMA(2) |
| Example B25 | First paste | Bis-GMA(60), TEGDMA(40) | CQ(0.20) | — | — | TBA(3) |
| | Second paste | Bis-GMA(60), TEGDMA(30), MHPA(10) | — | — | C14(1) | — |
| Example B26 | First paste | Bis-GMA(60), TEGDMA(40) | CQ(0.20) | — | — | DEAEMA(2) |
| | Second paste | Bis-GMA(60), TEGDMA(40) | — | — | C15(1) | — |
| Example B27 | First paste | Bis-GMA(60), TEGDMA(40) | CQ(0.20) | — | — | TBA(3) |
| | Second paste | D2.6E(70), TEGDMA(20), MHPA(10) | — | — | C13(10) | — |
| Example B28 | First paste | Bis-GMA(60), TEGDMA(40) | CQ(0.15) | — | — | TBA(3) |
| | Second paste | D2.6E(70), TEGDMA(20), MHPA(10) | — | — | C14(10) | — |
| Example B29 | First paste | Bis-GMA(60), TEGDMA(40) | CQ(0.10) | — | — | DMAEMA(2) |
| | Second paste | Bis-GMA(60), TEGDMA(40) | — | — | C15(10) | — |
| Example B30 | First paste | D2.6E(70), TEGDMA(20), MHPA(10) | CQ(0.10) | — | — | DEAEMA(0.8) |
| | Second paste | Bis-GMA(60), TEGDMA(40) | — | — | C1(1) | — |
| Example B31 | First paste | Bis-GMA(40), UDMA(30), TEGDMA(30) | CQ(0.10) | — | — | DEAEMA(0.8) |
| | Second paste | Bis-GMA(40), UDMA(30), TEGDMA(30) | — | — | C2(1) | — |
| Example B32 | First paste | Bis-GMA(40), UDMA(20), NPG(40) | CQ(0.10) | — | — | DEAEMA(0.8) |
| | Second paste | Bis-GMA(40), UDMA(20), NPG(40) | — | — | C1(10) | — |
| Example B33 | First paste | Bis-GMA(40), UDMA(20), NPG(40) | CQ(0.10) | — | — | DEAEMA(0.8) |
| | Second paste | Bis-GMA(40), UDMA(20), NPG(40) | — | — | C2(10) | — |
| Example B34 | First paste | Bis-GMA(60), TEGDMA(40) | CQ(0.10) | — | — | TBA(0.75) |
| | Second paste | Bis-GMA(60), TEGDMA(40) | — | — | C10(2.0) | — |
| Example B35 | First paste | Bis-GMA(40), UDMA(30), TEGDMA(30) | CQ(0.10) | — | — | TBA(2.0) |
| | Second paste | Bis-GMA(40), UDMA(30), TEGDMA(30) | — | — | C10(2.0) | — |
| Example B36 | First paste | Bis-GMA(60), TEGDMA(40) | CQ(0.10) | — | — | TBA(2.0) |
| | Second paste | Bis-GMA(60), TEGDMA(40) | — | — | C10(2.0) | — |
| Example B37 | First paste | Bis-GMA(40), UDMA(20), NPG(40) | CQ(0.10) | — | — | — |
| | Second paste | Bis-GMA(40), UDMA(20), NPG(40) | — | — | C10(2.0) | — |
| Example B38 | First paste | Bis-GMA(60), TEGDMA(40) | CQ(0.2) | — | — | DEAEMA(1.6) |
| | Second paste | Bis-GMA(60), TEGDMA(40) | — | — | C10(2.0) | — |
| Example B39 | First paste | Bis-GMA(60), TEGDMA(40) | CQ(0.2) | — | — | DEAEMA(1.6) |
| | Second paste | Bis-GMA(40), UDMA(30), TEGDMA(30) | — | — | C9(2.0) | — |
| Example B40 | First paste | Bis-GMA(40), UDMA(30), TEGDMA(30) | CQ(0.2) | — | — | TBA(1.6) |
| | Second paste | Bis-GMA(60), TEGDMA(40) | — | — | C4(2.0) | — |
| Example B41 | First paste | Bis-GMA(40), UDMA(20), NPG(40) | CQ(0.2) | — | — | — |
| | Second paste | Bis-GMA(40), UDMA(20), NPG(40) | — | — | C6(2.0) | — |
| Example B42 | First paste | Bis-GMA(40), UDMA(20), NPG(40) | CQ(0.2) | — | — | — |
| | Second paste | Bis-GMA(40), UDMA(20), NPG(40) | — | — | C8(2.0) | — |
| Example B43 | First paste | Bis-GMA(40), UDMA(20), NPG(40) | CQ(0.2) | — | — | — |
| | Second paste | Bis-GMA(40), UDMA(20), NPG(40) | — | — | C14(2.0) | — |
| Example B44 | First paste | Bis-GMA(40), UDMA(30), TEGDMA(30) | CQ(0.2) | — | — | — |
| | Second paste | Bis-GMA(40), UDMA(30), TEGDMA(30) | — | — | C15(2.0) | — |
| Example B45 | First paste | Bis-GMA(60), TEGDMA(40) | CQ(0.1) | — | — | TBA(2) |
| | Second paste | Bis-GMA(60), TEGDMA(40) | — | — | C11(2) | — |

TABLE 2-continued

| | | | | | | |
|---|---|---|---|---|---|---|
| Example B46 | First paste | Bis-GMA(60), TEGDMA(40) | — | — | — | DEAEMA(1.6) |
| | Second paste | Bis-GMA(60), TEGDMA(40) | CQ(0.1) | — | C7(1.5) | — |
| Example B47 | First paste | Bis-GMA(60), TEGDMA(40) | CQ(0.2) | — | — | TBA(2) |
| | Second paste | Bis-GMA(60), TEGDMA(40) | — | — | C11(2) | — |
| Example B48 | First paste | Bis-GMA(60), TEGDMA(40) | — | — | C8(2) | DBGE(1.6) |
| | Second paste | Bis-GMA(60), TEGDMA(40) | CQ(0.2) | — | — | — |
| Comparative Example CB1 | First paste | Bis-GMA(60), TEGDMA(40) | — | — | C7(4.0) | DMAEMA(2) |
| | Second paste | Bis-GMA(60), TEGDMA(40) | — | — | — | — |
| Comparative Example CB2 | First paste | Bis-GMA(60), TEGDMA(40) | CQ(0.4) | — | C7(1) | DMAEMA(2) |
| | Second paste | Bis-GMA(60), TEGDMA(40) | — | — | — | — |
| Comparative Example CB3 | First paste | Bis-GMA(60), TEGDMA(40) | CQ(0.6) | — | C7(2.0) | DMAEMA(2) |
| | Second paste | Bis-GMA(60), TEGDMA(40) | — | — | — | — |
| Comparative Example CB4 | First paste | Bis-GMA(60), TEGDMA(40) | CQ(0.8) | — | C7(2.0) | DMAEMA(2) |
| | Second paste | Bis-GMA(60), TEGDMA(40) | — | — | — | — |
| Comparative Example CB5 | First paste | Bis-GMA(60), TEGDMA(40) | CQ(0.2) | — | C4(0.7) | — |
| | Second paste | Bis-GMA(60), TEGDMA(40) | — | — | — | DEAEMA(2) |
| Comparative Example CB6 | First paste | Bis-GMA(60), TEGDMA(40) | CQ(0.2) | — | C9(2.0) | — |
| | Second paste | Bis-GMA(60), TEGDMA(40) | — | — | — | — |
| Comparative Example CB7 | First paste | Bis-GMA(60), TEGDMA(40) | CQ(0.3) | — | — | TBA(3) |
| | Second paste | Bis-GMA(60), TEGDMA(40) | — | — | C4(3) | — |
| Comparative Example CB8 | First paste | Bis-GMA(60), TEGDMA(40) | CQ(0.3) | — | — | TBA(3) |
| | Second paste | Bis-GMA(60), TEGDMA(40) | — | — | C8(3) | — |

| | | (D) Photopolymerization accelerator Other than (D-1) | (E) Filler | Chemical polymerization initiator or chemical polymerization accelerator | Others |
|---|---|---|---|---|---|
| Example B1 | First paste | — | Filler 1(100) | PTU(1.0) | BHT(0.2) |
| | Second paste | — | Filler 2(100) | CHP(1.5) | BHT(0.2) |
| Example B2 | First paste | — | Filler 2(100) | PTU(1.0) | MeHQ(0.01) |
| | Second paste | — | Filler 1(100) | CHP(1.5) | BHT(0.2) |
| Example B3 | First paste | — | Filler 1(100) | PTU(1), VOA(0.01) | MeHQ(0.005) |
| | Second paste | — | Filler 2(100) | CHP(1.5) | BHT(0.2) |
| Example B4 | First paste | — | Filler 2(100) | PTU(1), COA(0.1) | MeHQ(0.01) |
| | Second paste | — | Filler 1(100) | CHP(1.5) | BHT(0.2) |
| Example B5 | First paste | — | Filler 1(100) | PTU(1), COA(0.1) | MeHQ(0.005) |
| | Second paste | — | Filler 2(100) | CHP(1.5) | BHT(0.2) |
| Example B6 | First paste | — | Filler 1(100) | PTU(2), VOA(0.01) | MeHQ(0.01) |
| | Second paste | — | Filler 2(100) | CHP(3) | BHT(0.2) |
| Example B7 | First paste | — | Filler 2(100) | PTU(2), VOA(0.001) | MeHQ(0.005) |
| | Second paste | — | Filler 1(100) | CHP(3) | BHT(0.2) |
| Example B8 | First paste | — | Filler 2(100) | PTU(2), VOA(0.1) | MeHQ(0.01) |
| | Second paste | — | Filler 1(100) | CHP(3) | BHT(0.2) |
| Example B9 | First paste | — | Filler 2(100) | PTU(2), VOA(0.1) | MeHQ(0.01) |
| | Second paste | — | Filler 1(100) | CHP(3) | BHT(0.2) |
| Example B10 | First paste | — | Filler 2(100) | PTU(2), VOA(0.1) | MeHQ(0.01) |
| | Second paste | — | Filler 1(100) | CHP(3) | BHT(0.2) |
| Example B11 | First paste | — | Filler 2(100) | PTU(1), COA(0.01) | MeHQ(0.005) |
| | Second paste | — | Filler 2(100) | CHP(1.5) | BHT(0.2) |
| Example B12 | First paste | — | Filler 1(100) | PTU(1), COA(0.01) | MeHQ(0.01) |
| | Second paste | — | Filler 1(100) | CHP(1.5) | BHT(0.2) |
| Example B13 | First paste | — | Filler 2(100) | PTU(1), COA(0.01) | MeHQ(0.005) |
| | Second paste | — | Filler 2(100) | CHP(1.5) | BHT(0.2) |
| Example B14 | First paste | — | Filler 1(100) | PTU(1), COA(0.01) | MeHQ(0.005) |
| | Second paste | — | Filler 2(100) | CHP(1.5) | BHT(0.2) |
| Example B15 | First paste | — | Filler 1(100) | PTU(1), COA(0.01) | MeHQ(0.005) |
| | Second paste | — | Filler 1(100) | CHP(1.5) | BHT(0.2) |
| Example B16 | First paste | — | Filler 2(100) | PTU(1), COA(0.01) | BHT(0.2) |
| | Second paste | — | Filler 2(100) | CHP(1.5) | BHT(0.2) |
| Example B17 | First paste | MDEOA(0.4) | Filler 1(100) | PTU(1), COA(0.01) | MeHQ(0.005) |
| | Second paste | — | Filler 1(100) | CHP(1.5) | BHT(0.2) |
| Example B18 | First paste | TEA(0.4) | Filler 1(100) | PTU(1), COA(0.01) | MeHQ(0.005) |
| | Second paste | — | Filler 2(100) | CHP(1.5) | BHT(0.2) |
| Example B19 | First paste | — | Filler 2(100) | PTU(1), COA(0.01) | MeHQ(0.005) |
| | Second paste | — | Filler 1(100) | CHP(1.5) | BHT(0.2) |
| Example B20 | First paste | — | Filler 1(100) | PTU(1), VOA(0.01) | MeHQ(0.005) |
| | Second paste | — | Filler 2(100) | CHP(1.5) | BHT(0.2) |
| Example B21 | First paste | — | Filler 2(100) | PTU(1), COA(0.1) | MeHQ(0.01) |
| | Second paste | — | Filler 1(100) | CHP(1.5) | BHT(0.2) |
| Example B22 | First paste | — | Filler 1(250) | PTU(1), COA(0.01) | MeHQ(0.02) |
| | Second paste | — | Filler 2(250) | CHP(1.5) | BHT(0.1) |
| Example B23 | First paste | — | Filler 1(250) | PTU(1), COA(0.01) | MeHQ(0.02) |
| | Second paste | — | Filler 2(250) | CHP(1.5) | BHT(0.1) |
| Example B24 | First paste | — | Filler 1(250) | PTU(1.6), COA(0.01) | MeHQ(0.02) |
| | Second paste | — | Filler 2(250) | CHP(1.8) | BHT(0.1) |
| Example B25 | First paste | — | Filler 2(250) | PTU(2) | MeHQ(0.02) |
| | Second paste | — | Filler 2(250) | CHP(3) | BHT(0.1) |

TABLE 2-continued

| | | | | | |
|---|---|---|---|---|---|
| Example B26 | First paste | — | Filler 1(250) | PTU(2), VOA(0.005) | MeHQ(0.02) |
| | Second paste | — | Filler 1(250) | CHP(3) | BHT(0.1) |
| Example B27 | First paste | — | Filler 2(250) | PTU(2) | MeHQ(0.02) |
| | Second paste | — | Filler 1(250) | CHP(3) | BHT(0.1) |
| Example B28 | First paste | — | Filler 2(250) | PTU(2), VOA(0.005) | MeHQ(0.02) |
| | Second paste | — | Filler 1(250) | CHP(3) | BHT(0.1) |
| Example B29 | First paste | — | Filler 2(250) | PTU(2) | MeHQ(0.02) |
| | Second paste | — | Filler 1(250) | CHP(3) | BHT(0.1) |
| Example B30 | First paste | — | Filler 2(250) | PTU(2), VOA(0.005) | MeHQ(0.02) |
| | Second paste | — | Filler 1(250) | CHP(3) | BHT(0.1) |
| Example B31 | First paste | — | Filler 2(250) | PTU(2) | MeHQ(0.02) |
| | Second paste | — | Filler 1(250) | CHP(3) | BHT(0.1) |
| Example B32 | First paste | — | Filler 2(250) | PTU(2), VOA(0.005) | MeHQ(0.02) |
| | Second paste | — | Filler 1(250) | CHP(3) | BHT(0.1) |
| Example B33 | First paste | DMBE(0.3) | Filler 1(250) | PTU(2), VOA(0.005) | MeHQ(0.02) |
| | Second paste | — | Filler 2(250) | CHP(3) | BHT(0.1) |
| Example B34 | First paste | DMBE(0.5) | Filler 2(250) | PTU(1.5), VOA(0.005) | MeHQ(0.02) |
| | Second paste | — | Filler 1(250) | CHP(2) | BHT(0.1) |
| Example B35 | First paste | DMPT(0.5) | Filler 1(250) | PTU(1.5), VOA(0.005) | MeHQ(0.02) |
| | Second paste | — | Filler 2(250) | CHP(2) | BHT(0.1) |
| Example B36 | First paste | DEPT(0.5) | Filler 1(250) | PTU(1.5), VOA(0.005) | MeHQ(0.02) |
| | Second paste | — | Filler 1(250) | CHP(2) | BHT(0.1) |
| Example B37 | First paste | DEPT(0.5) | Filler 1(250) | PTU(1.5), VOA(0.005) | MeHQ(0.02) |
| | Second paste | — | Filler 1(250) | CHP(2) | BHT(0.1) |
| Example B38 | First paste | — | Filler 1(400) | PTU(1.5), VOA(0.005) | — |
| | Second paste | — | Filler 1(400) | CHP(2) | — |
| Example B39 | First paste | — | Filler 1(400) | CHP(2) | — |
| | Second paste | — | Filler 1(400) | PTU(1.5), VOA(0.005) | — |
| Example B40 | First paste | — | Filler 1(400) | PTU(1.6), COA(0.01) | — |
| | Second paste | — | Filler 1(400) | CHP(1.8) | — |
| Example B41 | First paste | TEA(1) | Filler 1(400) | CHP(2) | — |
| | Second paste | — | Filler 1(400) | PTU(1.5), VOA(0.005) | — |
| Example B42 | First paste | MDEOA(1) | Filler 1(400) | PTU(1.6), COA(0.01) | — |
| | Second paste | — | Filler 1(400) | CHP(1.8) | — |
| Example B43 | First paste | MDEOA(1) | Filler 1(400) | PTU(1.6), COA(0.01) | — |
| | Second paste | — | Filler 1(400) | CHP(1.8) | — |
| Example B44 | First paste | MDEOA(1) | Filler 1(400) | PTU(1.6), COA(0.01) | — |
| | Second paste | — | Filler 1(400) | CHP(1.8) | — |
| Example B45 | First paste | — | Filler 2(100) | DEPT(1.5) | — |
| | Second paste | — | Filler 1(100) | BPO(1.5) | BHT(0.2) |
| Example B46 | First paste | — | Filler 1(250) | DEPT(1.5) | MeHQ(0.02) |
| | Second paste | — | Filler 2(250) | BPO(1.5) | BHT(0.1) |
| Example B47 | First paste | — | Filler 1(400) | COA(0.5), VOA(0.01) | BHT(0.1) |
| | Second paste | — | Filler 1(400) | BPO(1.5) | BHT(0.2) |
| Example B48 | First paste | — | Filler 1(400) | DEPT(1.5) | — |
| | Second paste | — | Filler 1(400) | BPO(1.5) | BHT(0.2) |
| Comparative Example CB1 | First paste | — | Filler 2(250) | PTU(1.6), COA(0.01) | MeHQ(0.005) |
| | Second paste | — | Filler 2(250) | CHP(1.8) | — |
| Comparative Example CB2 | First paste | — | Filler 1(100) | PTU(1.6), COA(0.01) | MeHQ(0.005) |
| | Second paste | — | Filler 1(100) | CHP(1.8) | — |
| Comparative Example CB3 | First paste | — | Filler 2(400) | PTU(1.6), COA(0.01) | MeHQ(0.005) |
| | Second paste | — | Filler 2(400) | CHP(1.8) | — |
| Comparative Example CB4 | First paste | — | Filler 1(250) | CHP(2) | MeHQ(0.005) |
| | Second paste | — | Filler 1(250) | PTU(1.5), VOA(0.005) | — |
| Comparative Example CB5 | First paste | — | Filler 2(250) | CHP(2) | MeHQ(0.005) |
| | Second paste | — | Filler 2(250) | PTU(1.5), VOA(0.005) | — |
| Comparative Example CB6 | First paste | — | Filler 2(250) | CHP(2) | MeHQ(0.005) |
| | Second paste | — | Filler 2(250) | PTU(1.5), VOA(0.005) | — |
| Comparative Example CB7 | First paste | — | Filler 1(80) | CHP(2) | MeHQ(0.005) |
| | Second paste | — | Filler 1(80) | PTU(1.5), VOA(0.005) | — |
| Comparative Example CB8 | First paste | — | — | CHP(2) | MeHQ(0.005) |
| | Second paste | — | — | PTU(1.5), VOA(0.005) | — |

The test methods adopted in Examples and Comparative Examples are as follows. For one pack type dental photocurable composition, the dental photo-curable composition was directly collected. For two packs type dental photocurable composition, a paste prepared by mixing the first paste and the second paste using a mixing tip manufactured by Mixpack Co., Ltd. was used.

(1) Flexural Strength

The prepared dental photocurable composition was filled into a stainless steel mold, and the cover glasses were placed on both sides to press with a glass kneading plate. Thereafter, light was irradiated for 10 seconds to 5 locations by using the photopolymerization irradiator (PEN Bright manufactured SHOFU Inc.) to cure the dental curable composition. After curing, the cured product was removed from the mold, and light was irradiated to the backside in the same manner again to use as a test specimen (25×2×2 mm rectangular shape). For one pack type dental photocurable composition, the test specimen was immersed in water at 37° C. for 24 hours, and thereafter flexural test was performed. For two packs type dental photocurable composition, flexural test was performed within 1 hour after irradiating the test specimen with light. The flexural test was conducted at a distance between supporting points of 20 mm and at a crosshead speed of 1 mm/min using an Instron universal testing machine (manufactured by Instron).

Evaluation criteria for flexural strength of the one pack type dental photocurable composition and the two packs type dental photocurable composition is as follows.
Good: 100 MPa or more
Applicable: 80 MPa or more and less than 100 MPa
Insufficient: less than 80 MPa
(2) Difference in Color Tone Between Before Photo-Curing and after Photo-Curing Each prepared dental photocurable composition was fully filled into a mold (in a shape of a disc having a diameter of 15 mm and a thickness of 1 mm) made of stainless steel. Thereafter, a cover glass that is colorless and transparent has a thickness of 170 µm or less was placed on upper side of the stainless mold to apply pressure with glass plate. After confirming that the dental photocurable composition was in a uniform state without containing air bubbles, the color tone before curing was measured. Subsequently light irradiation was performed for 1 minutes using a photopolymerization irradiator (Grip Light II, manufactured by Shofu Inc.) via the cover glass to prepare a cured material and the cured material was taken out of the mold and was measured for color tone. Color measurement was performed by placing the test specimen on the background of a standard white plate (D65/10°, X=81.07, Y=86.15, Z=93.38) and using a spectrocolorimeter (manufactured by BYK-Chemie GmbH) under predetermined condition (light source: C, viewing angle: 2°, measurement area: 11 mm). From the color measurement results, the difference in color tone before photocuring and after photocuring was evaluated from the value b*before curing and the value b*after curing. The value b* corresponds to blue to yellow, and the higher the value b*, the greater the yellowness. Generally since a light source of 400 to 500 nm, particularly 450 to 490 nm is used for dental materials, the photosensitizer has absorption at 400 to 500 nm. Therefore, the value b* increases proportional to the compounding amount of the photosensitizer. On the other hand, if the color tone of the photosensitizer disappears after polymerization, the value b* decreases. Moreover, since the discoloration of dental materials is often yellow or reddish brown, the change in color tone can be evaluated from the change in the value b*. In the present disclosure, evaluation criteria for Δb* indicating the change value of b* between before curing and after curing is as follows.
Good: Δb* was less than 4
Applicable: Δb* was 4 or more and 5 or less than
Insufficient: Δb* was more than 5

When Δb* exceeds 5, it was determined that the color tone change between before curing and after curing was large and the color tone after curing could not be predicted from the color tone before curing. On the other hand, when Δb* was 5 or less, it was determined that the color tone change between before curing and after curing was small and the color tone after curing could be predicted from the color tone before curing. Further, the value b* after curing is preferably less than 7, more preferably less than 6. When the value b* after curing is less than 7, it can be used in a clinical case that are suitable for tooth with less yellowness, and it particularly can be used for white dental material that is separately compounded with a white pigment such as titanium oxide.

(3) Light Color Stability

Each prepared dental photocurable composition was fully filled into a mold (in a shape of a disc having a diameter of 15 mm and a thickness of 1 mm) made of stainless steel. Thereafter, a cover glass that is colorless and transparent was placed on upper side of the stainless mold to apply pressure with glass plate. Subsequently, light irradiation was performed for 1 minutes using a photopolymerization irradiator (Grip Light II, manufactured by SHOFU Inc.) via the cover glass to prepare a cured material. The cured material was taken out of the mold, the cover glass was removed and the test specimen was measured for color tone. Color measurement was performed by placing the test specimen on the background of a standard white plate (D65/10°, X=81.07, Y=86.15, Z=93.38) and using a spectrocolorimeter (manufactured by BYK-Chemie GmbH) under predetermined condition (light source: C, viewing angle: 2°, measurement area: 11 mm). Then, after exposing the test specimen to light for 24 hours with a xenon lamp light exposure tester (Suntest CPS+), the color tone of the test specimen was measured again, and the difference in discoloration was represented by ΔE calculated from the following formula.

$$\Delta E = ((\Delta L^*)^2 + (\Delta a^*)^2 + (\Delta b^*)^2)^{1/2}$$

$$\Delta L^* = L1^* - L2^*$$

$$\Delta a^* = a1^* - a2^*$$

$$\Delta b^* = b1^* - b2^*$$

In the formula, L1* is the brightness index before light exposure, L2* is the brightness index after light exposure, a1* and b1* are the color quality index before light exposure, and a2* and b2* are the color quality index after light exposure. Evaluation criteria is as follows.
Good: ΔE was less than 5
Applicable: ΔE was 5 or more and 10 or less than
Insufficient: ΔE was more than 10

When the light color stability is good, discoloration is small in the case of using the dental material in the oral cavity for a long period of time, and a highly aesthetic property can be maintained.

(4) Thermal Color Stability

Each prepared dental photocurable composition was fully filled into a mold (in a shape of a disc having a diameter of 15 mm and a thickness of 1 mm) made of stainless steel. Thereafter, a cover glass that is colorless and transparent was placed on upper side of the stainless mold to apply pressure with glass plate. Subsequently, light irradiation was performed for 1 minutes using a photopolymerization irradiator (Grip Light II, manufactured by SHOFU Inc.) via the cover glass to prepare a cured material. The cured material was taken out of the mold, the cover glass was removed and the test specimen was measured for color tone. Color measurement was performed by placing the test specimen on the background of a standard white plate (D65/10°, X=81.07, Y=86.15, Z=93.38) and using a spectrocolorimeter (manufactured by BYK-Chemie GmbH) under predetermined condition (light source: C, viewing angle: 2°, measurement area: 11 mm). Then, the test specimen was immersed in 10 mL of water in a container in an incubator set at 70° C., allowed to stand for one week, and was measured again for the color tone, and the difference in discoloration was represented by ΔE calculated from the following formula.

$$\Delta E = ((\Delta L^*)^2 + (\Delta a^*)^2 + (\Delta b^*)^2)^{1/2}$$

$$\Delta L^* = L1^* - L2^*$$

$$\Delta a^* = a1^* - a2^*$$

$$\Delta b^* = b1^* - b2^*$$

In the formula, L1* is the brightness index before immersion and stand, L2* is index after immersion and stand, a1* and b1* are the color quality index before immersion and stand, and a2* and b2* are the color quality index after immersion and stand. Evaluation criteria is as follows.
Good: ΔE was less than 5
Applicable: ΔE was 5 or more and 10 or less than
Insufficient: ΔE was more than 10

When the thermal stability is good, discoloration is small in the case of using the dental material in the oral cavity for a long period of time, and a highly aesthetic state can be maintained for a long period of time.

The results shown in Tables 3 and 4 will be described.

TABLE 3

|  | Flexural strength (Mpa) | Result of Color measurement ||||
|---|---|---|---|---|---|---|
|  |  | Before curing b* | After curing b* | Difference in color tone Δb* | Light color stability | Thermal color stability |
| Example A1 | 85 | 2.9 | 2.8 | 0.1 | 0.5 | 0.6 |
| Example A2 | 89 | 4.2 | 3.1 | 1.1 | 0.6 | 0.6 |
| Example A3 | 122 | 4.6 | 3.2 | 1.4 | 0.8 | 1.7 |
| Example A4 | 106 | 4.2 | 3.2 | 1.0 | 0.8 | 1.0 |
| Example A5 | 106 | 6.7 | 3.8 | 2.9 | 1.3 | 0.9 |
| Example A6 | 122 | 7.1 | 3.8 | 3.3 | 1.4 | 1.3 |
| Example A7 | 114 | 7.8 | 3.9 | 3.9 | 4.8 | 1.0 |
| Example A8 | 118 | 8.7 | 3.8 | 4.9 | 5.5 | 1.6 |
| Example A9 | 85 | 6.8 | 4.0 | 2.8 | 1.7 | 1.7 |
| Example A10 | 85 | 6.9 | 4.4 | 2.5 | 1.8 | 0.7 |
| Example A11 | 124 | 8.8 | 6.0 | 2.8 | 2.7 | 1.7 |
| Example A12 | 128 | 9.0 | 6.8 | 2.2 | 4.4 | 1.7 |
| Example A13 | 130 | 12.5 | 9.9 | 2.6 | 9.1 | 0.6 |
| Example A14 | 84 | 6.5 | 3.0 | 3.5 | 2.1 | 0.8 |
| Example A15 | 82 | 6.7 | 3.9 | 2.8 | 1.6 | 1.0 |
| Example A16 | 108 | 6.8 | 4.3 | 2.5 | 2.3 | 0.7 |
| Example A17 | 106 | 8.0 | 5.9 | 2.1 | 5.1 | 0.9 |
| Example A18 | 122 | 9.8 | 7.5 | 2.3 | 5.4 | 1.1 |
| Example A19 | 119 | 14.7 | 9.9 | 4.8 | 10.9 | 3.2 |
| Example A20 | 114 | 7.2 | 6.2 | 1.0 | 15.0 | 0.8 |
| Example A21 | 102 | 7.3 | 6.0 | 1.3 | 15.9 | 0.6 |
| Example A22 | 105 | 8.0 | 6.2 | 1.8 | 4.2 | 1.8 |
| Example A23 | 109 | 8.9 | 6.0 | 2.9 | 4.9 | 1.6 |
| Example A24 | 113 | 6.7 | 3.8 | 2.9 | 2.1 | 4.9 |
| Example A25 | 117 | 6.9 | 5.0 | 1.9 | 2.3 | 8.4 |
| Example A26 | 115 | 7.0 | 5.4 | 1.6 | 2.0 | 9.9 |
| Example A27 | 126 | 7.6 | 3.9 | 3.6 | 2.2 | 1.3 |
| Example A28 | 110 | 4.8 | 2.1 | 2.6 | 1.7 | 1.2 |
| Example A29 | 83 | 6.4 | 4.4 | 2.0 | 4.4 | 0.6 |
| Example A30 | 83 | 6.9 | 4.9 | 2.0 | 4.2 | 1.5 |
| Example A31 | 83 | 7.0 | 4.9 | 2.1 | 4.6 | 0.5 |
| Example A32 | 102 | 9.5 | 7.7 | 1.8 | 10.2 | 1.1 |
| Example A33 | 103 | 10.1 | 8.9 | 1.2 | 10.7 | 1.0 |
| Example A34 | 128 | 9.8 | 7.8 | 2.0 | 11.1 | 1.4 |
| Example A35 | 98 | 5.0 | 2.3 | 2.7 | 1.9 | 1.1 |
| Example A36 | 97 | 4.7 | 3.2 | 1.5 | 2.4 | 1.8 |
| Example A37 | 111 | 5.1 | 3.7 | 1.4 | 7.5 | 2.1 |
| Example A38 | 121 | 4.8 | 3.5 | 1.3 | 8.0 | 3.2 |
| Example A39 | 106 | 4.7 | 2.6 | 2.1 | 2.4 | 9.8 |
| Example A40 | 118 | 5.2 | 2.8 | 2.4 | 2.0 | 8.1 |
| Example A41 | 114 | 4.9 | 2.9 | 2.0 | 1.7 | 9.9 |
| Example A42 | 108 | 5.1 | 3.0 | 2.1 | 2.4 | 7.8 |
| Example A43 | 106 | 4.5 | 2.8 | 1.7 | 11.8 | 0.7 |
| Example A44 | 120 | 4.9 | 3.2 | 1.7 | 9.9 | 1.6 |
| Example A45 | 122 | 4.8 | 4.9 | −0.1 | 7.5 | 8.6 |
| Example A46 | 111 | 4.8 | 5.2 | −0.4 | 7.3 | 8.6 |
| Example A47 | 127 | 4.7 | 4.4 | 0.3 | 1.1 | 0.9 |
| Example A48 | 84 | 2.0 | 1.8 | 0.2 | 1.9 | 0.6 |
| Example A49 | 94 | 4.0 | 3.9 | 0.1 | 1.4 | 0.7 |
| Example A50 | 129 | 8.8 | 4.4 | 4.4 | 5.6 | 1.1 |
| Example A51 | 120 | 11.6 | 7.0 | 4.6 | 12.2 | 0.8 |
| Example A52 | 126 | 4.0 | 3.1 | 0.9 | 12.2 | 1.0 |
| Example A53 | 113 | 4.8 | 3.4 | 1.4 | 15.3 | 1.2 |
| Example A54 | 128 | 5.2 | 3.7 | 1.5 | 1.3 | 0.9 |
| Example A55 | 123 | 5.5 | 2.9 | 2.6 | 1.7 | 0.7 |
| Example A56 | 126 | 5.2 | 2.8 | 2.4 | 1.2 | 0.6 |
| Example A57 | 128 | 5.7 | 3.1 | 2.6 | 1.3 | 9.6 |
| Example A58 | 124 | 5.6 | 3.4 | 2.2 | 1.7 | 8.2 |
| Example A59 | 128 | 5.6 | 3.4 | 2.2 | 10.2 | 0.9 |
| Example A60 | 80 | 2.7 | 2.7 | 0.0 | 0.4 | 0.3 |
| Example A61 | 131 | 12.8 | 10.2 | 2.6 | 9.8 | 2.0 |
| Example A62 | 134 | 4.6 | 4.3 | 0.3 | 1.9 | 1.4 |
| Example A63 | 139 | 4.6 | 4.4 | 0.2 | 2.1 | 1.6 |
| Example A64 | 100 | 6.4 | 4.8 | 1.6 | 3.9 | 1.8 |
| Example A65 | 132 | 4.9 | 3.5 | 1.4 | 4.9 | 1.8 |
| Example A66 | 81 | 2.9 | 2.8 | 0.1 | 0.4 | 0.4 |

TABLE 3-continued

| | Flexural strength (Mpa) | Result of Color measurement | | | | |
|---|---|---|---|---|---|---|
| | | Before curing b* | After curing b* | Difference in color tone Δb* | Light color stability | Thermal color stability |
| Example A67 | 115 | 10.3 | 7.9 | 2.4 | 7.8 | 3.0 |
| Example A68 | 118 | 4.6 | 3.0 | 1.6 | 1.2 | 2.1 |
| Example A69 | 109 | 6.5 | 4.0 | 2.5 | 1.1 | 0.4 |
| Example A70 | 120 | 8.0 | 5.5 | 2.5 | 3.2 | 1.6 |
| Comparative Example CA1 | Uncured | Uncured | Uncured | Uncured | Uncured | Uncured |
| Comparative Example CA2 | 110 | 9.7 | 4.4 | 5.2 | 6.9 | 1.0 |
| Comparative Example CA3 | 118 | 11.4 | 3.6 | 7.8 | 9.7 | 0.8 |
| Comparative Example CA4 | 107 | 14.8 | 5.7 | 9.2 | 9.0 | 0.9 |
| Comparative Example CA5 | 59 | 2.7 | 2.8 | 0.0 | 1.4 | 1.6 |
| Comparative Example CA6 | 60 | 3.2 | 1.0 | 2.2 | 1.6 | 1.4 |
| Comparative Example CA7 | 83 | 10.5 | 3.9 | 6.6 | 6.9 | 1.1 |
| Comparative Example CA8 | 91 | 10.2 | 4.0 | 6.2 | 1.3 | 0.6 |
| Comparative Example CA9 | 92 | 14.1 | 2.4 | 11.7 | 5.5 | 0.8 |
| Comparative Example CA10 | 82 | 12.6 | 2.6 | 10.0 | 1.5 | 0.6 |
| Comparative Example CA11 | 66 | 6.0 | 7.0 | −1.0 | 5.3 | 1.1 |
| Comparative Example CA12 | 120 | 15.1 | 6.8 | 8.3 | 8.7 | 11.4 |

TABLE 4

| | Flexural strength (Mpa) | Result of Color measurement | | | | |
|---|---|---|---|---|---|---|
| | | Before curing b* | After curing b* | Difference in color tone Δb* | Light color stability | Thermal color stability |
| Example B1 | 84 | 2.9 | 2.8 | 0.1 | 0.5 | 1.1 |
| Example B2 | 82 | 4.3 | 2.9 | 1.4 | 0.6 | 1.3 |
| Example B3 | 120 | 4.4 | 3.0 | 1.4 | 0.8 | 1.2 |
| Example B4 | 107 | 4.5 | 3.0 | 1.5 | 0.8 | 0.9 |
| Example B5 | 125 | 8.6 | 3.7 | 4.9 | 5.7 | 1.1 |
| Example B6 | 83 | 6.9 | 4.1 | 2.8 | 1.7 | 1.6 |
| Example B7 | 85 | 6.8 | 4.3 | 2.6 | 2.0 | 1.4 |
| Example B8 | 105 | 7.6 | 6.0 | 1.6 | 2.5 | 1.0 |
| Example B9 | 113 | 8.8 | 6.5 | 2.3 | 1.9 | 1.2 |
| Example B10 | 114 | 10.1 | 8.9 | 1.2 | 8.7 | 1.7 |
| Example B11 | 84 | 6.3 | 3.1 | 3.2 | 1.9 | 1.7 |
| Example B12 | 82 | 6.6 | 4.0 | 2.6 | 2.0 | 1.6 |
| Example B13 | 125 | 8.9 | 6.7 | 2.2 | 6.8 | 1.0 |
| Example B14 | 102 | 10.1 | 8.8 | 1.3 | 5.9 | 0.9 |
| Example B15 | 125 | 14.8 | 10.0 | 4.8 | 10.9 | 1.2 |
| Example B16 | 104 | 6.5 | 3.9 | 2.6 | 1.5 | 4.9 |
| Example B17 | 120 | 7.0 | 5.0 | 2.0 | 2.5 | 8.2 |
| Example B18 | 119 | 6.9 | 5.3 | 1.6 | 2.4 | 9.8 |
| Example B19 | 114 | 7.5 | 3.7 | 3.8 | 1.9 | 1.6 |
| Example B20 | 129 | 4.6 | 3.3 | 1.3 | 2.2 | 1.1 |
| Example B21 | 103 | 4.9 | 3.2 | 1.7 | 2.3 | 1.5 |
| Example B22 | 107 | 5.2 | 3.0 | 2.2 | 2.2 | 1.2 |
| Example B23 | 104 | 5.0 | 2.9 | 2.1 | 1.7 | 1.4 |
| Example B24 | 84 | 6.6 | 4.1 | 2.5 | 4.0 | 1.1 |
| Example B25 | 83 | 6.8 | 4.8 | 2.0 | 4.8 | 1.3 |
| Example B26 | 81 | 7.1 | 4.9 | 2.2 | 4.2 | 0.8 |
| Example B27 | 120 | 9.7 | 7.5 | 2.1 | 11.1 | 1.1 |
| Example B28 | 122 | 9.9 | 9.0 | 0.9 | 8.5 | 1.0 |
| Example B29 | 128 | 9.9 | 7.8 | 2.1 | 10.4 | 0.6 |
| Example B30 | 94 | 4.8 | 2.3 | 2.6 | 2.1 | 1.4 |
| Example B31 | 94 | 4.5 | 3.3 | 1.2 | 1.6 | 0.7 |
| Example B32 | 92 | 5.2 | 3.8 | 1.4 | 4.2 | 1.4 |
| Example B33 | 112 | 4.9 | 3.3 | 1.5 | 9.8 | 1.1 |
| Example B34 | 122 | 4.3 | 2.9 | 1.4 | 11.8 | 0.7 |

TABLE 4-continued

| | Flexural strength (Mpa) | Before curing b* | After curing b* | Difference in color tone Δb* | Light color stability | Thermal color stability |
|---|---|---|---|---|---|---|
| | | | | Result of Color measurement | | |
| Example B35 | 105 | 4.9 | 3.0 | 1.9 | 9.9 | 1.3 |
| Example B36 | 121 | 5.0 | 4.8 | 0.2 | 7.2 | 8.9 |
| Example B37 | 103 | 5.2 | 4.6 | 0.6 | 7.6 | 9.1 |
| Example B38 | 102 | 5.0 | 2.5 | 2.5 | 1.9 | 1.8 |
| Example B39 | 120 | 5.0 | 2.5 | 2.5 | 1.9 | 0.7 |
| Example B40 | 112 | 5.1 | 2.4 | 2.6 | 1.9 | 0.8 |
| Example B41 | 125 | 5.0 | 3.1 | 1.9 | 2.9 | 9.9 |
| Example B42 | 114 | 5.1 | 3.2 | 1.9 | 3.9 | 8.1 |
| Example B43 | 111 | 5.2 | 3.5 | 1.7 | 7.2 | 7.6 |
| Example B44 | 117 | 4.9 | 3.6 | 1.3 | 7.6 | 7.8 |
| Example B45 | 108 | 4.9 | 3.2 | 1.7 | 7.3 | 9.4 |
| Example B46 | 119 | 5.0 | 2.9 | 2.1 | 7.6 | 9.0 |
| Example B47 | 127 | 4.9 | 3.6 | 1.3 | 1.9 | 1.1 |
| Example B48 | 117 | 4.9 | 3.6 | 1.3 | 7.6 | 9.6 |
| Comparative Example CB1 | Uncured | Uncured | Uncured | Uncured | Uncured | Uncured |
| Comparative Example CB2 | 119 | 10.0 | 4.6 | 5.4 | 6.7 | 0.7 |
| Comparative Example CB3 | 104 | 11.3 | 4.0 | 7.3 | 5.7 | 0.5 |
| Comparative Example CB4 | 124 | 14.9 | 5.5 | 9.3 | 6.5 | 0.7 |
| Comparative Example CB5 | 62 | 3.0 | 2.2 | 0.8 | 1.1 | 0.8 |
| Comparative Example CB6 | 48 | 3.4 | 1.0 | 2.4 | 1.7 | 0.6 |
| Comparative Example CB7 | 81 | 10.0 | 4.1 | 6.0 | 5.8 | 0.6 |
| Comparative Example CB8 | 83 | 14.3 | 2.6 | 11.7 | 5.7 | 1.2 |

The compositions described in the examples had Δb* less than 5 and 80 MPa or more of flexural strength, and therefore the color change between before curing and after curing was sufficiently small, and the compositions had mechanical strength sufficient to be compatible with dental material.

In Examples A1, A60, A66, and B1, because the compounding amount of the α-diketone compound was small, there was a tendency that flexural strength was low. On the other hand, in Examples A8, A19, A50, A51, B5 and B15, because the compounding amount of the α-diketone compound was large, there was a tendency that the value b* before curing and the value b* after curing were large.

In Examples A9, A60, A66, and B6, because the compounding amount of the photoacid generator was small, there was a tendency that flexural strength was low. On the other hand, in Examples A13, A19, A51, A61, and B10, because the compounding amount of the photoacid generator was large, there was a tendency that although the flexural strength was high, the light color stability decreased and the value b* after curing increased.

In Examples A29 to A34 and B24 to B29, the aryliodonium salt contained as a photoacid generator in the composition was an aryliodonium salt other than a salt of an anion having an organic group and one or more atoms of P, B, Al, S, and Ga, and an aryl iodonium cation. In Examples A29 to A31 and B24 to B26 in which the compounding amount of the photoacid generator was relatively small, there was a tendency that the flexural strength was low, and the light color stability was slightly lowered. In Examples A32 to A34 and B27 to B29 in which the compounding amount of the photoacid generator was relatively large, there was a tendency that the light color stability was further lowered, and the value b* after curing was increased. In Example 69 and Example 70 in which the aryliodonium salt contained as a photoacid generator was a salt of an anion having an organic group and one or more atoms of P, B, Al, S, and Ga, and an aryl iodonium cation, there was a tendency that the decrease of light color stability and the increase of the value b* were suppressed.

In Examples A35 to A38 and B31 to B34, the aryliodonium salt contained as a photoacid generator in the composition was a salt of an anion having an organic group in which at least one H was substituted with F and one or more atoms of P, B, Al, S, and Ga, and an aryl iodonium cation. In Examples A35, A36, B31, and B32 in which the compounding amount of the photoacid generator was relatively small, there was a tendency that flexural strength was low. In Examples A37, A38, B33, and B34 in which the compounding amount of the photoacid generator was relatively large, there was a tendency that the light color stability decreased. In Example 69 and Example 70, in which the aryliodonium salt contained as a photoacid generator was a salt of an anion having an organic group and one or more atoms of P, B, Al, S, and Ga, and an aryl iodonium cation, there was a tendency that the decrease of light color stability was suppressed.

In Examples A14, A48, A66, and B11, because the compounding amount of the photopolymerization accelerator is small, there is a tendency that flexural strength was low. On the other hand, in Examples A18, A67, and B14, because the compounding amount of the photopolymerization accelerator was large, there was a tendency that the light color stability decreased and b* after curing increased.

Examples A20 to A23, A43 to A46A52, A53, A59, A65, B34 to B37 contained an aromatic amine as photopolymerization accelerators. For example, in Examples A20, A21, B34, and B35 there was a tendency that light color stability was poor. On the other hand, when the ultraviolet absorbers were compounded such as Examples A22 and A23, there was a tendency that the decrease in light color stability was suppressed. However, it is preferable that an ultraviolet absorber was not compounded because a large amount of the ultraviolet absorber may cause an increase in the value b* and a decrease in mechanical strength. In addition, in Example A65 containing only 0.01 parts by mass of aromatic amine, photocolor stability was good.

In Examples A24 to A26, A39 to A43, B16 to B18, and B41 to B44, an aliphatic amine having a primary hydroxy group was contained. Examples A24 and B16 in which DBAE having one primary hydroxy group in the molecule was contained were in a particularly good range although the thermal color stability tended to decrease slightly. In Examples A25, A26, A39 to A43, B17, B18, and B41 to B44 containing MDEOA having two primary hydroxy groups in the molecule or TEA having three primary hydroxy groups in the molecule, there was a tendency that thermal color stability was significantly poor. In addition, in Examples A45, A46, B36 and B37 containing DEPT having two primary hydroxy groups in the molecule, there was also a tendency that thermal color stability was poor. In Examples B45, B46, and B48 compounded as a chemical polymerization accelerator, there was the same tendency. Even when compounded as a chemical polymerization accelerator, it may also function as a photopolymerization accelerator.

In Comparative Example CA1 and Comparative Example CB1 in which no α-diketone was compounded, sufficient curability was not exhibited. In Comparative Example CA11 in which BAPO was contained as a photosensitizer instead of the α-diketone compound, flexural strength was insufficient. In Comparative Examples CA2 to CA4 and CB2 to CB4 in which the compounding amount of the α-diketone compound was large, Δb* between before curing and after curing exceeded 5 and therefore these were sufficient. In Comparative Examples CA5 and CB5 in which the compounding amount of the photoacid generator was small and Comparative Examples CA6 and CB6 in which the photoacid generator was not compounded, the flexural strength was not sufficient. In Comparative Examples CA7 to CA10 and CB7 and CB8 in which the compounding amount of the filler was small or the filler was not compounded, although flexural strength was sufficiently high and there was no problem in curability Δb* between before curing and after curing exceeded 5 and therefore these were sufficient.

The dental photocurable composition of the present disclosure evaluated in Examples can be used for any known dental photocurable composition without any problem. The dental photocurable composition of the present disclosure may be used for a dental adhesive material, a dental composite resin, a dental core build-up material, a dental resin cement, a dental coating material, a dental sealant material, a dental manicure material, a dental splinting material, a dental glass ionomer cement, a dental hard resin, a dental CAD-CAM restoration material, a dental 3D printer material and the like.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this invention without difficulty. Accordingly any such changes and modifications are intended to be included in the scope of the embodiments.

INDUSTRIAL APPLICABILITY

According to the present disclosure, it is possible to provide a dental photocurable composition having sufficient mechanical property and being excellent in color tone selectivity because of having a small color difference between before curing and after curing.

What is claimed is:

1. A dental photocurable composition, comprising (A) polymerizable monomer, (B) photosensitizer, (C) photoacid generator, (D) photopolymerization accelerator and (E) filler, wherein,
    the dental photocurable composition comprises (B-1) α-diketone compound as the (B) photosensitizer, and
    the dental photocurable composition comprises, with respect to 100 parts by mass of the (A) polymerizable monomer,
        0.15 parts by mass or less of the (B-1) α-diketone compound,
        0.5 parts by mass or more of the (C) photoacid generator, and
        100 parts by mass or more of the (E) filler.

2. The dental photocurable composition according to claim 1, wherein
    the (B-1) α-diketone compound is a camphorquinone compound.

3. The dental photocurable composition according to claim 1, wherein
    the dental photocurable composition comprises an aryl iodonium salt as the (C) photoacid generator, wherein
    the aryl iodonium salt is a salt of an anion having an organic group and one or more atoms of P, B, Al, S and Ga, and an aryl iodonium cation.

4. The dental photocurable composition according to claim 1, wherein
    the dental photocurable composition comprises an aryl iodonium salt as the (C) photoacid generator, wherein
    the aryl iodonium salt is a salt of an anion having an organic group in which at least one H is substituted with F and one or more atoms of P, B, Al, S and Ga, and an aryl iodonium cation.

5. The dental photocurable composition according to claim 1, wherein
    the dental photocurable composition comprises (D-1) aliphatic tertiary amine compound not having two or more primary hydroxy groups as the (D) photopolymerization accelerator.

6. The dental photocurable composition according to claim 1, wherein
    the dental photocurable composition comprises, with respect to 100 parts by mass of the (A) polymerizable monomer,
        1 parts by mass or more of the (C) photoacid generator, and
        0.5 parts by mass or more of the (D) photopolymerization accelerator.

7. The dental photocurable composition according to claim 1, wherein
    a difference between a b* value before curing which is obtained by color measuring a color tone in the L*a*b* color space for a 1-mm-thick dental photocurable composition, excluding a pigment where the dental photocurable composition contains the pigment, on a white background and a b* value after curing which is obtained by color measuring a color tone in the L*a*b* color space for a 1-mm-thick cured body of the dental photocurable composition on a white background is 5 or less.

8. The dental photocurable composition according to claim 1, wherein
the dental photocurable composition is a one pack type dental photocurable composition comprising, with respect to 100 parts by mass of the (A) polymerizable monomer,
0.005 to 0.15 parts by mass of the (B-1) α-diketone compound,
0.5 to 10 parts by mass of the (C) photoacid generator,
0.1 to 10.0 parts by mass of the (D) photopolymerization accelerator, and
150 to 1000 parts by mass or more of the (E) filler.

9. The dental photocurable composition according to claim 1, wherein
the dental photocurable composition is a two packs type dental photocurable composition consisting of a first paste and a second paste, wherein
the first paste includes a first matrix containing the (A) polymerizable monomer, the (B-1) α-diketone compound, the (C) photoacid generator and the (D) photopolymerization accelerator, and the (E) filler,
the second paste includes a second matrix containing the (A) polymerizable monomer, the (B-1) α-diketone compound, the (C) photoacid generator and the (D) photopolymerization accelerator, and the (E) filler,
a specific gravity of the first paste and the second paste is 1:0.8 to 1:1.2,
the dental photocurable composition comprises, with respect to 200 parts by mass of a total of the (A) polymerizable monomer contained in the first matrix and the second matrix,
0.01 to 0.3 parts by mass of the (B-1) α-diketone compound,
1.0 to 20.0 parts by mass of the (C) photoacid generator,
0.2 to 20.0 parts by mass of the (D) photopolymerization accelerator, and
200 to 800 parts by mass or more of the (E) filler.

10. The dental photocurable composition according to claim 1, wherein
the dental photocurable composition constitutes a dental kit by using in combination with a dental composition used for checking color conformity.

11. The dental photocurable composition according to claim 2, wherein
the dental photocurable composition comprises an aryl iodonium salt as the (C) photoacid generator, wherein
the aryl iodonium salt is a salt of an anion having an organic group in which at least one H is substituted with F and one or more atoms of P, B, Al, S and Ga, and an aryl iodonium cation.

12. The dental photocurable composition according to claim 11, wherein
the dental photocurable composition comprises (D-1) aliphatic tertiary amine compound not having two or more primary hydroxy groups as the (D) photopolymerization accelerator.

13. The dental photocurable composition according to claim 12, wherein
the dental photocurable composition comprises, with respect to 100 parts by mass of the (A) polymerizable monomer,
1 parts by mass or more of the (C) photoacid generator, and
0.5 parts by mass or more of the (D) photopolymerization accelerator.

14. The dental photocurable composition according to claim 13, wherein
a difference between a b* value before curing which is obtained by color measuring a color tone in the L*a*b* color space for a 1-mm-thick dental photocurable composition, excluding a pigment where the dental photocurable composition contains the pigment, on a white background and a b* value after curing which is obtained by color measuring a color tone in the L*a*b* color space for a 1-mm-thick cured body of the dental photocurable composition on a white background is 5 or less.

15. The dental photocurable composition according to claim 14, wherein
the dental photocurable composition is a one pack type dental photocurable composition comprising, with respect to 100 parts by mass of the (A) polymerizable monomer,
0.005 to 0.15 parts by mass of the (B-1) α-diketone compound,
0.5 to 10 parts by mass of the (C) photoacid generator,
0.1 to 10.0 parts by mass of the (D) photopolymerization accelerator, and
150 to 1000 parts by mass or more of the (E) filler.

16. The dental photocurable composition according to claim 14, wherein
the dental photocurable composition is a two packs type dental photocurable composition consisting of a first paste and a second paste, wherein
the first paste includes a first matrix containing the (A) polymerizable monomer, the (B-1) α-diketone compound, the (C) photoacid generator and the (D) photopolymerization accelerator, and the (E) filler,
the second paste includes a second matrix containing the (A) polymerizable monomer, the (B-1) α-diketone compound, the (C) photoacid generator and the (D) photopolymerization accelerator, and the (E) filler,
a specific gravity of the first paste and the second paste is 1:0.8 to 1:1.2,
the dental photocurable composition comprises, with respect to 200 parts by mass of a total of the (A) polymerizable monomer contained in the first matrix and the second matrix,
0.01 to 0.3 parts by mass of the (B-1) α-diketone compound,
1.0 to 20.0 parts by mass of the (C) photoacid generator,
0.2 to 20.0 parts by mass of the (D) photopolymerization accelerator, and
200 to 800 parts by mass or more of the (E) filler.

17. The dental photocurable composition according to claim 15, wherein
the dental photocurable composition constitutes a dental kit by using in combination with a dental composition used for checking color conformity.

18. The dental photocurable composition according to claim 16, wherein
the dental photocurable composition constitutes a dental kit by using in combination with a dental composition used for checking color conformity.

19. The dental photocurable composition according to claim 1, wherein
the dental photocurable composition does not contain an aromatic amine compound.

20. The dental photocurable composition according to claim 16, wherein
the dental photocurable composition contains a tertiary amine compound as the (D) photopolymerization accelerator.

\* \* \* \* \*